US006841361B1

(12) United States Patent
Oka et al.

(10) Patent No.: US 6,841,361 B1
(45) Date of Patent: Jan. 11, 2005

(54) METHODS OF PRODUCING RECOMBINANT INSULIN FROM NOVEL FUSED PROTEINS

(75) Inventors: Shusaku Oka, Ibaraki (JP); Seiji Sato, Ibaraki (JP); Naohiko Higashikuni, Ibaraki (JP); Masaaki Kondo, Ibaraki (JP); Toshiyuki Kudo, Ibaraki (JP); Shigeaki Watanabe, Ibaraki (JP); Yoshihiro Waki, Ibaraki (JP); Hirotaka Yuki, Ibaraki (JP)

(73) Assignee: Itoham Foods Inc., Kobe (JP)

( * ) Notice: Subject to any disclaimer, the term of this patent is extended or adjusted under 35 U.S.C. 154(b) by 0 days.

(21) Appl. No.: 09/959,548

(22) PCT Filed: Apr. 26, 2000

(86) PCT No.: PCT/JP00/02736

§ 371 (c)(1),
(2), (4) Date: Jan. 28, 2002

(87) PCT Pub. No.: WO00/66738

PCT Pub. Date: Nov. 9, 2000

(30) Foreign Application Priority Data

Apr. 30, 1999 (JP) ........................................ 1999-124877

(51) Int. Cl.$^7$ ................................................ C12P 21/04
(52) U.S. Cl. ...................................................... 435/69.7
(58) Field of Search ................................. 530/300, 350; 435/69.1, 69.7, 320.1, 69.9; 514/1; 526/23.1

(56) References Cited

U.S. PATENT DOCUMENTS

| | | | |
|---|---|---|---|
| 4,431,740 A | | 2/1984 | Bell et al. |
| 4,994,380 A | | 2/1991 | Udaka et al. |
| 5,149,716 A | | 9/1992 | Vertesy et al. |
| 5,378,613 A | * | 1/1995 | Belagaje .................... 435/69.7 |
| 5,426,036 A | * | 6/1995 | Koller et al. .............. 435/69.7 |
| 5,473,049 A | | 12/1995 | Obermeier et al. |
| 5,663,291 A | | 9/1997 | Obermeier et al. |
| 5,962,267 A | * | 10/1999 | Shin et al. ................. 435/69.4 |
| 6,001,604 A | * | 12/1999 | Hartman et al. ........... 435/69.4 |

FOREIGN PATENT DOCUMENTS

| | | |
|---|---|---|
| EP | 0055945 A2 | 7/1982 |
| EP | 0531530 A1 | 3/1990 |
| EP | 0704527 | 4/1996 |
| EP | A2 704527 | 4/1996 |
| GB | 2 072 680 | 10/1981 |
| JP | A11-341991 | 12/1999 |
| JP | 11-341991 | 12/1999 |
| WO | 96/20724 | 7/1996 |
| WO | A 96/32489 | 10/1996 |
| WO | WO96/32489 | 10/1996 |
| WO | WO 97/03089 A2 | 1/1997 |

OTHER PUBLICATIONS

Yamagata H, Adachi T, Tsuboi A, Takao M, Sasaki T, Tsukagoshi N, Udaka S. Cloning and characterization of the 5' region o the cell wall protein gene operon in Bacillus brevis 47.J Bacteriol. Mar. 1987;169(3):1239–45.*

Nilsson et al., Journal of Biotechnology, 48 pp. 241–250 (1996).

Simonson et al., Human Gene Therapy, vol. 7, pp. 71–78 (Jan. 1, 1996).

Groskreutz et al., The Journal of Biological Chemistry, vol. 269, No. 8, pp. 6241–6245 (Feb. 25, 1994).

Udaka et al., Methods in Enzymology, vol. 217, pp. 23–33 (1993).

Miyauchi et al., Journal of Industrial Microbiology & Biotechnology, vol. 21, pp. 208–214 (1998).

Hideo Yamagata et al., "Cloning and Characterization of the 5' Region of the Cell Wall Protein Gene Operon in Bacillus brevis 47", Journal of Bacteriology, vol. 169(3) Mar. 1987, pp. 1239–1245.

Makoto Takao et al., "Production of swine pepsinogen by protein–producing Bacillus brevis carrying swine pepsinogen cDNA", Appl. Microbiol. Biotechnol., vol. 30, 1989, pp. 75–80.

Hideo Yamagata et al., "Use of Bacillus brevis for efficient synthesis and secretion of human epidermal growth factor", Proc. Natl. Acad. Sci. USA, vol. 86, May 1989, pp. 3589–3593.

* cited by examiner

Primary Examiner—Karen Cochrane Carlson
Assistant Examiner—Sheridan K Snedden
(74) Attorney, Agent, or Firm—Birch, Stewart, Kolasch & Birch, LLP

(57) ABSTRACT

This invention relates to a DNA encoding a fusion protein of formula (I)

$$[Y]-[X1]-[B\text{-chain}]-[X2]-[Linker]-[X3]-[A\text{-chain}] \qquad (I)$$

wherein

Y is a leader peptide sequence for the expression and secretion of the protein, comprising at least one amino acid residue;

X1 is an amino acid sequence which is cleavable enzymatically or chemically;

B-chain is the amino acid sequence of insulin B chain;

X2 is an amino acid sequence which is cleavable enzymatically;

Linker is a linker sequence comprising at least one amino acid residue;

X3 is an amino acid sequence which is cleavable enzymatically; and

A- chain is the amino acid sequence of insulin A chain, and to a method for producing insulin using an expression system containing the DNA in high efficiency and high yield.

18 Claims, 10 Drawing Sheets

Fig.2

**MWPsp-MWPmp9-GSLQPR-Bchain-RGHRP-Linker-PR pNU-mPINS: X=MWPsp-MWPmp9-GSLQPR-B chain-RGHRP-Linker-PR-A chain

METHODS OF PRODUCING RECOMBINANT INSULIN FROM NOVEL FUSED PROTEINS

This application is the national phase under 35 U.S.C. §371 of PCT International Application No. PCT/JP00/02736 which has an International filing date of Apr. 26, 2000, which designated the United States of America.

BACKGROUND OF THE INVENTION

1. Technical Field

The present invention relates to a DNA encoding a novel fusion protein which is used for preparing recombinant insulin. More specifically, the present invention relates to the use of the DNA for the preparation of insulin from the fusion protein, which is obtained by the expression of the DNA, through the action of thrombin and carboxypeptidase B.

2. Background Art

Insulin is a hormone secreted by the B cells of the islet of Langerhans in the pancreas when an animal ingests food, which is the most important hormone for storage or use of sugars, amino acids and fatty acids and for maintaining the blood sugar homeostasis. Although blood sugar, namely glucose in blood, is an essential energy source for a living body, if the blood sugar homeostasis is not maintained, then serious conditions may develop. Increased blood sugar level causes the excretion of sugar in the urine, resulting in loss of glucose, i.e. onset of a so-called diabetes. If this condition continues for long periods, complications can develop in the tissues of a living body. On the other hand, decreased blood sugar level leads to an insufficient supply of the energy source, resulting in imperilment of life. Homeostasis of the blood sugar level is maintained by balancing factors that act to increase the blood sugar level (e.g., glucagon, growth hormone, cortisol, catecholamine) with factors that act to decrease the blood sugar level. Insulin is the only hormone which can decrease the blood sugar level. Hence, the reduction in secretion functions resulted from some causes and, as a consequence, insufficient supply of insulin can induce insulin-dependent diabetes mellitus (IDDM). For patients suffering from such a disease, insulin is an indispensable drug.

Human insulin is a polypeptide comprising an A chain with 21 amino acids and a B chain with 30 amino acids, which has one intrachain disulfide bond in the A chain and two disulfide bonds which link between the A chain and the B chain. Insulin is initially biosynthesized as "preproinsulin" on ribosomes in B cells of the islets of Langerhans of the pancreas. Preproinsulin is a linear molecule comprising a signal peptide with 24 amino acids (SP), a B chain (B), a C-peptide with 31 amino acids (C) and an A chain (A) linked in the order as represented by the formula "SP-B-C-A". Upon transport to the endoplasmic reticulum, the signal peptide is cleaved out from the preproinsulin to produce "proinsulin (B-C-A)". Proinsulin forms disulfide bonds in the endoplasmic reticulum, thereby taking on a three-dimensional structure. Proinsulin is cleaved with a prohormone-converting enzyme PC1/3 at the B-C junction and then cleaved with a converting enzyme PC2 at the C-A junction. Finally, N-terminal two basic amino acid residues of the C-peptide, which remain at the C-terminus of the B-chain when cleaved with PC1/3, are cut out with carboxypeptidase H. In this manner, insulin is produced.

Methods for producing therapeutic insulin have been initially developed using extracts from the pancreas of animals such as bovine and pig. However, human insulin is different in amino acid composition from bovine insulin (at two positions in A chain and one position in B chain) and porcine insulin (at one position in B chain). Therefore, adverse effects (e.g., allergy) are inevitable in the use of bovine or porcine insulin in human bodies. Methods for semi-synthesis of human insulin from porcine insulin have been developed which utilize the transpeptidation reaction with trypsin. However, recombinant insulin produced by genetic recombinant techniques has currently gone mainstream due to its low production cost and good production efficiency.

For the production of recombinant insulin, a number of methods have been developed. For example, the method developed by Eli Lilly Corp. is known, which method comprises expressing A chain and B chain separately using *Escherichia coli*; and mixing the A chain and the B chain in vitro to form the disulfide bridges, thereby linking them via the disulfide bonds (JP-B- 63-18960). This method, however, is poor in production efficiency. Then, Eli Lilly Corp. has developed an improved method which comprises expressing proinsulin; forming the disulfide bonds in vitro; and then cleaving out the C-peptide from the product with trypsin and carboxypeptidase B, thereby producing insulin (JP-B-1-48278 and Japanese Patent No. 2634176).

Another method was developed by Novo Nordisk Corp., which method comprises expressing miniproinsulin comprising a B chain and an A chain linked via two basic amino acid residues, in yeast; and then treating the miniproinsulin with trypsin in vitro, thereby producing insulin (JP-B-7-121226 and JP-B-8-8871, and Japanese Patent No.2553326). This method has such advantages that the disulfide bonds are formed during the expression and secretion of the miniproinsulin and that the miniproinsulin can be isolated and purified readily because it is secreted into a cultured medium.

Development of new recombinant insulin-production methods has been continued positively. Hoechst Corporation developed a method comprising expressing a new-type insulin derivative or preproinsulin in *E. coli*; forming the disulfide bonds in vitro; and then treating the product with lysylendopeptidase or clostripain/carboxypeptidase B, thereby producing insulin (JP-A-2-195896, JP-A-2-225498, JP-A-2-233698, JP-A-3-169895, JP-A4-258296, JP-A-6-228191, and JP-A-7-265092). Recently, a method has been developed by BIO-TECHNOLOGY GENERAL CORPORATION, in which a fusion protein comprising superoxide dismutase (SOD) linked with proinsulin is expressed in *E. coli* to increase both the expression efficiency and the disulfide bond-forming efficiency, and proinsulin is converted into insulin with trypsin and carboxypeptidase B (WO 96/20724). Thus, there are a number of approaches for recombinant insulin production, and further improvement has been made in expression efficiency, disulfide bond-forming efficiency and conversion into insulin.

As the hosts for the production of recombinant proteins, a wide variety of hosts have been used including microorganisms, animals and plants. Among them, microorganisms are most frequently used due to their easy-to-handle property and good applicability for industrial use, and *Escherichia coil* and yeast are especially known. Recently, an expression system with *Bacillus brevis* has been known for recombinant proteins (see Japanese Patent No. 2082727; JP-A-62-201583; Yamagata, H. et al., J. Bacteriol. 169:1239–1245, 1987; Juzo Udaka, Nihon Nogei Kagaku-shi 61, 669–676, 1987; Takao, M. et al., Appi. Microbiol. Biotechnol. 30:75–80, 1989; Yamagata, H. et al., Proc. Natl. Acad. Sci. USA 86:3589–3593, 1989).

The object of the present invention is to develop an expression system and a production method for insulin which have a high yield and a production efficiency equal to or better than those of the existing recombinant insulin production systems. That is, the object of the present invention is to develop a novel method for converting an insulin precursor into insulin, an environment where the disulfide bonds necessary for insulin activity can be formed, and an expression system with high yield.

SUMMARY OF THE INVENTION

In one aspect of the present invention, there is provided a DNA encoding a fusion protein of formula (1):

[Y]-[X1]-[B-chain]-[X2]-[Linker]-[X3]-[A-chain]    (I)

wherein
- Y is a leader peptide sequence for expression and secretion of the protein, comprising at least one amino acid residue;
- X1 is an amino acid sequence which is cleavable enzymatically or chemically;
- B-chain is the amino acid sequence of insulin B chain;
- X2 is an amino acid sequence which is cleavable enzymatically;
- Linker is a linker sequence comprising at least one amino acid residue;
- X3 is an amino acid sequence which is cleavable enzymatically; and
- A-chain is the amino acid sequence of insulin A chain, and wherein the Y, X1, B-chain, X2, Linker, X3 and A-chain are ligated in the order indicated in formula (I).

In another aspect of the present invention, the present invention is provide a DNA encoding a fusion protein of formula (II):

[B-chain]-[X2]-[Linker]-[X3]-[A-chain]    (II)

wherein:
- B-chain is the amino acid sequence of insulin B chain;
- X2 is an amino acid sequence which is cleavable enzymatically;
- Linker is a linker sequence comprising at least one amino acid residue;
- X3 is an amino acid sequence which is cleavable enzymatically; and
- A-chain is the amino acid sequence of insulin A chain, and wherein the B-chain, X2, Linker, X3 and A-chain are ligated in the order indicated in formula (II).

In one embodiment of the present invention, the amino acid sequence X1, X2 or X3, which is used for enzymatic cleavage of a fusion protein, is a sequence cleavable with thrombin. For example, the amino acid sequence which is cleavable with thrombin is the following sequence:
- X1=GlySerLeuGlnProArg (SEQ ID NO:1);
- X2=ArgGlyHisArgPro (SEQ ID NO:2); or
- X3=ProArg.

In another embodiment of the present invention, the linker sequence has the following amino acid sequence:
GluAlaGluAspLeuGlnValGlyGln-
ValGluLeuGlyGlyGlyProGlyAlaGlySer
LeuGlnProLeuAlaLeuGluGlySerLeuGln (SEQ ID NO:3).

In still another embodiment of the present invention, the leader peptide sequence may comprise N-terminal 9 amino acid residues (i.e., the amino acid positions 1 to 9) of the protein MWP which is one of the cell wall proteins (CWPS) derived from a bacterium belonging to the genus Bacillus. In this case, the DNA may comprise a CWP signal peptide attached at the 5' end of the DNA.

An example of the DNA of the present invention is a DNA comprising a nucleotide sequence encoding an amino acid sequence shown in SEQ ID NO:21. More specifically, the DNA comprises a nucleotide sequence shown in SEQ ID NO:20.

In another aspect of the present invention, there is provided a DNA comprising a DNA sequence which comprises a promoter region required for the expression of a recombinant protein in a prokaryote or eukaryote, the DNA sequence being attached at the 5' end of the DNA defined above.

In an embodiment of the present invention, the DNA sequence which comprises a promoter region is derived from a bacterium belonging to the genus Bacillus, and is preferably derived from the CWP from a bacterium belonging to the genus Bacillus.

In another aspect of the present invention, there is provided a vector containing the DNA defined above.

In still another aspect of the present invention, there is provided a host cell transformed with the vector. The host cell is preferably a bacterium belonging to the genus Bacillus, such as *Bacillus brevis*.

In still another aspect of the present invention, there is provided a method for producing insulin, wherein the method comprises:
- culturing the host cell or bacterium in a culture medium, to express a fusion protein encoded by a DNA of interest in the host cell or bacterium;
- collecting the fusion protein; and
- subjecting the fusion protein to an enzymatic cleavage treatment to isolate insulin.

In this aspect, an example of the DNA is a DNA comprising a nucleotide sequence shown in SEQ ID NO:21, and an example of the fusion protein is a protein comprising an amino acid sequence shown in SEQ ID NO:22.

In the method, the expressed fusion protein may be separated and purified from the host cell or the bacteria or the cultured medium. According to an embodiment of the present invention, the enzymatic cleavage may be performed with thrombin and carboxypeptidase B.

BRIEF DESCRIPTION OF THE DRAWINGS

FIG. 2 is the amino acid sequence of a fusion protein MWPmp9-GSLQPR-Bchain-RGHRP-Linker-PR-Achain and the nucleotide sequence encoding the same.

DETAILED DESCRIPTION

Figure 1:
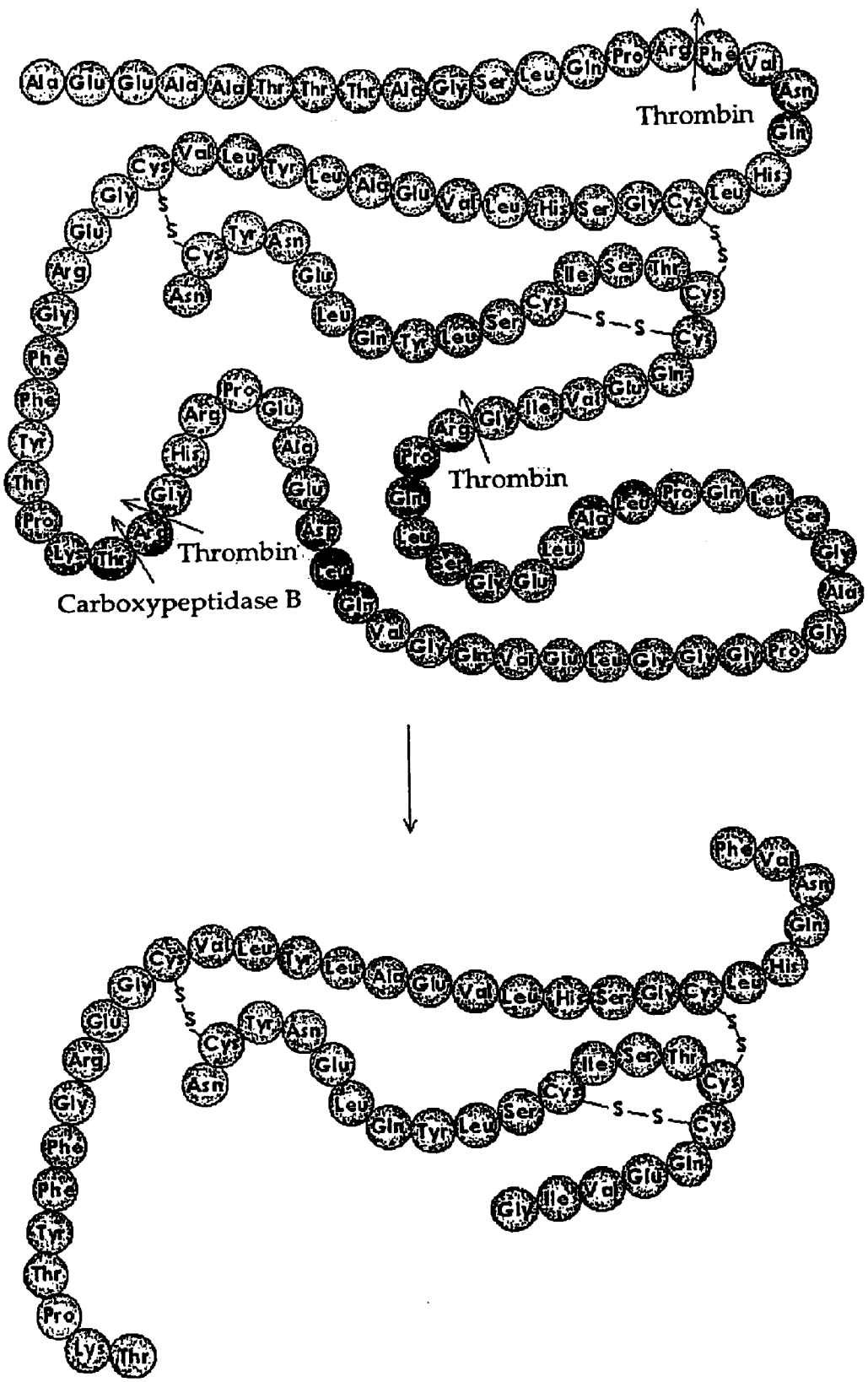
FIG. 1 illustrates the conversion of a fusion protein MWPmp9-GSLQPR-Bchain-RGHRP-Linker-PR-Achain into insulin.

The DNA of the present invention has the structure represented by the above formula (I) or (It). The DNA of formula (I) comprises a leader peptide sequence for expression and secretion of a fusion protein of interest, comprising at least one amino acid residue (Y); an amino acid sequence which is cleavable enzymatically or chemically (X1); a amino acid sequence of insulin B chain (B-chain); an amino acid sequence which is cleavable enzymatically (X2); a linker sequence comprising at least one amino acid residue (Linker); an amino acid sequence which is cleavable enzymatically (X3); and an amino acid sequence of insulin A chain (A-chain), wherein the Y, X1, B-chain, X2, Linker, X3, and A-chain are ligated in this order. The DNA of formula (II) comprises a amino acid sequence of insulin B chain (B-chain); an amino acid sequence which is cleavable enzymatically (X2); a linker sequence comprising at least one amino acid residue (Linker); an amino acid sequence which is cleavable enzymatically (X3); and an amino acid sequence of insulin A chain (A-chain), wherein the B-chain, X2, Linker, X3, and A-chain are ligated in this order. The presence of the leader peptide sequence enables to secrete the expression product outside the host cell, while the absence thereof provides the accumulation of the expression product within the host cell.

In the examples described below, for establishment of a method for converting the fusion protein into insulin with thrombin and carboxypeptidase B, a novel modified proinsulin is designed in which thrombin-cleavage sites are provided between the insulin B chain and the linker peptide and between the linker peptide and the insulin A chain. The modified proinsulin is then linked at its N-terminus, with the N-terminal 9-amino acids of a cell wall protein (CWP) from Bacillus brevis as a leader peptide, and a third thrombin-cleavage site which enables the cleavage of the modified proinsulin from the leader peptide is further linked immediately after the leader peptide, thereby providing an environment for forming disulfide bonds and enabling the expression of the modified proinsulin in Bacillus brevis. In this manner, the linear artificial fusion protein which comprises a leader peptide, a thrombin-cleavage site, insulin B chain, a thrombin-cleavage site, a linker peptide, a thrombin-cleavage site, and insulin A chain in the order, can be designed. At first, a DNA encoding the corresponding fusion protein was prepared and inserted into a suitable expression vector. The vector is then introduced into a suitable host cell. The transformed host cell is cultured to express the DNA, thereby producing the fusion protein. The fusion protein is then enzymatically cleaved with thrombin and carboxypeptidase B. Thus, insulin having the desired primary structure and biological activity, which are identical with those of the naturally occurring insulin, can be produced.

The present invention will be illustrated in more detail hereinafter.

The leader peptide (Y), which comprises at least one amino acid residue required for the expression of a protein of interest, includes the known MBP (Maina, C.V. et al., Gene 74:365–373, 1988), GST (Smith, D. B., et al., Gene 67:31–40, 1988), TRX (La Vallie, E. R. et al., Bio/Technology 11:187–193, 1993), DsbA (Collins-Racie, L.A. et al., Bio/Technology 13:982–987, 1995) and LamB (Benson, S. A. et al., Cell 32:1325–1335, 1983), which are derived from E. coli; and α factor derived from yeast (Brake, A. J., Yeast Genetic Engineering, p269–280, 1989). In particular, the leader sequence is often required, for E. coli, when a protein of interest is secreted into the periplasm or, for yeast, when the protein is secreted into the culture medium. According to an embodiment of the present invention, a preferred leader peptide comprises the N-terminal 9 amino acids of a CWP from a bacterium belonging to the genus Bacillus (hereinafter, sometimes referred to as "Bacillus bacterium"). The CWP useful for the present invention includes, but is not limited to, those derived from Bacillus brevis strain 47 (FERM P-7224; JP-A-60-58074 and JP-A-62-201589), strain HPD 31 (FERM BP-1087; 1P-A- 4-278091). Specifically, the following sequences may be used (where the brackets show references).

MWPmp9: AlaGluGluAlaAlaThrThrThrAla (SEQ ID NO:4; J. Bacteriol., 169:1239–1245, 1989)

OWPmp9: AlaProLysAspGlylleTyrIleGly (SEQ ID NO:5; J. Bacteriol., 170:176–186, 1988)

HWPmp9: AlaGluAspThrThrThrAlaProLys (SEQ ID NO:6; J. Bacteriol., 172:1312–1320, 1990)

The number of amino acid residues from the N-termninus of the CWP is not necessary to be 9, as long as the fusion protein can be expressed. For example, a sequence comprising N-terminal 1–50 amino acid residues of the CWP from a Bacillus bacterium may be used. The leader peptide is not always be needed if the fusion protein portion behind insulin B chain of the fusion protein, namely [B-chain]-[X2]-[Linker]-[X3]-[A-chain], is linked with the 3' end of a DNA containing the promoter region of an expression system to enable the expression of the fusion protein portion. When the fusion protein contains a leader peptide derived from a CWP, it is preferred that the leader peptide is linked to a CWP (particularly MWP) signal peptide at its 5' end. The information regarding MWP sequences can be found in Yamagata, H. et al., J. Bacteriol., 169:1239–1245, 1987 or Tsuboi, A. et al., J. Bacteriol., 170:935–945, 1988, and one can refer to them. The signal peptide generally helps to direct an expressed and translated protein to a cell membrane and to secrete the protein extracellularly. A secreted protein is advantageous because it can be more readily isolated and purified compared to non-secreted protein.

For the fusion protein, the enzymatic cleavage of X1 includes the use of an enzyme of which no cleavage site is contained in insulin B chain or insulin A chain, such as factor Xa, thrombin and enterokinase. When a Gly or Ser residue is attached to the N-terminus of insulin B chain, if such a residue has no influence to the activity of the resulting insulin, then TEV protease may be used. On the other hand, the chemical cleavage of the X1may include a selective cleavage at the C-terminus of methionine (J. Biol. Chem., 237:1856–1860, 1962) and a selective cleavage at the C-terminus of tryptophan (Methods in Enzymol., 91:318–324, 1983). According to a preferred embodiment of the present invention, all of X1 to X3 may be cleaved simultaneously, in which the enzyme used is thrombin and the amino acid sequences of X1 to X3 are as follows: X1=GlySerLeuGlnProArg (SEQ ID NO:1); X2=ArgGlyHisArgPro (SEQ ID NO:2); and X3=ProArg. In this case, X1, X2 and X3 with other amino acid sequences may also be employed, provided that the intended cleavage with thrombin can be achieved. For example, in the above amino acid sequences, the following substitutions are possible for such cleavage: for X1 and X3, Ser=Val, Glu, Phe, Asp, Pro, Ileu, Gly, Lys, Arg, Ala, Gln, Asn or Leu; Leu=Arg, Val, Phe, Asp, Gly, Leu, His, Ileu, Met, Thr or Lys; Gln=Gln, Phe, Tyr, Gly, Ileu, Asn, Ala, Arg, Thr, Ser. Leu, Val or Cys; Pro=Ala or Val; and Arg=Lys (SEQ ID NO:22; Chang, J-Y, Eur. J. Biochem., 151:217–224, 1985; Kawabata, S. et al., Eur. J. Biochem., 172:17–25, 1988); and for X2, Arg=Lys; Gly=Thr, Ileu, His, Ser, Ala, Phe, Val, Asn, Asp, Leu or Pro; His=Pro, Trp, Cys, Gln, Thr, Ser, Val, Leu, Ala, Phe or Gly; Arg =Val, Pro, Glu, Asn, Asp, Ser, Met, Lys, Ala, Gln, Gly, Trp or Thr; Pro =Val, Thr, Leu, Ser, Asp, Gly, Tyr, Ileu, Asn, Arg, His or Glu (SEQ ID NO:23; Chang, J-Y, Eur. J. Biochem., 151:217–224, 1985).

The linker comprising at least one amino acid residue is usually present between functional domains in a protein and can joint the domains without no influence on the fuictions of the domains. enzymatically cleavable sequence, and serves for the formation of disulfide bonds between insulin B chain and insulin A chain and for the readily expression of the fusion protein. The linker may comprise at least one amino acid residue and any kind of amino acid(s) may be used, provided that it exerts the same function. According to a preferred embodiment of the present invention, the linker may preferably comprise the C peptide of proinsulin. According to an embodiment of the present invention, the linker comprises the following sequence:

GluAlaGluAspLeuGlnValGlyGln-ValGluLeuGlyGlyGlyProGlyAlaGlySer LeuGlnProLeuAlaLeuGluGlySerLeuGln (SEQ ID NO:3).

In the present invention, the DNA encoding the fusion protein is expressed in the form linked with the 3' end of a DNA containing a promoter region for an expression system employed. Examples of the promoter include bacteriophage λpL promoter, T7 promoter, *E. coli* trp-lac promoter (Maniatis, T. et al., Molecular Cloning 2nd ed., A Laboratory Manual, Cold Spring Harbor Laboratory, 1989), yeast PRBI promoter (BIO/TECHNOLOGY 9:183–187, 1991), GAPDH promoter (BIO/TECHNOLOGY 12:381–384, 1994), viral LTR promoter, SV40 promoter (Maniatis, T. et al., Molecular Cloning 2nd ed., A Laboratory Manual, Cold Spring Harbor Laboratory, 1989). According to an embodiment of the present invention, the fusion protein is linked with the 3' end of a DNA-sequence containing a promoter region derived from a Bacillus bacterium. The available promoter includes, but is not limited to, MWP promoter derived from *Bacillus brevis* strain 47 (JP-A-1-58950 and JP-A-7-108224), HWP promoter derived from *Bacillus brevis* strain HPD31 (JP-A-4-278091 and JP-A-6-133782).

The DNA of the present invention may be prepared by any combination of the techniques known in the art. For example, constituent DNA sequences of the DNA may be prepared separately by chemical synthesis methods or cloning methods and ligated in sequence with a ligase, and the resulting DNA sequence may be subjected to polymerase chain reaction (PCR) in combination, thereby producing the intended DNA. The details of the specific preparation method for the DNA will be appreciated with reference to the examples below. In the preparation of the DNA, conventional techniques may be employed, such as those described in Maniatis, T. et al., Molecular Cloning 2nd ed., A Laboratory Manual, Cold Spring Harbor Laboratory, 1989; and Innis, M. A. et al., PCR Protocols, A guide to methods and applications, Academic Press, 1990.

The DNA encoding human insulin comprising insulin B chain, C peptide and A chain may be obtained from a commercially available human pancreas-derived mRNA using commercially available cDNAlst-strand synthesis kit (Pharmacia) or the like. When short-strand DNAs (as primers) can be synthesized based on known DNA sequences using a commercially available DNA synthesizer, the DNA fragments encoding the B chain, the C peptide and the A chain may be amplified by a conventional PCR method. In this case, the PCR may be performed for 20 cycles or more under the following conditions: DNA denaturation (e.g., at 94° C. for 30 sec.–1 min.); annealing to the primer (e.g., at about 45–60° C. for 30 sec.–1 min.); and elongation reaction (e.g., at 72° C. for 30 sec. or more).

Figure 3:
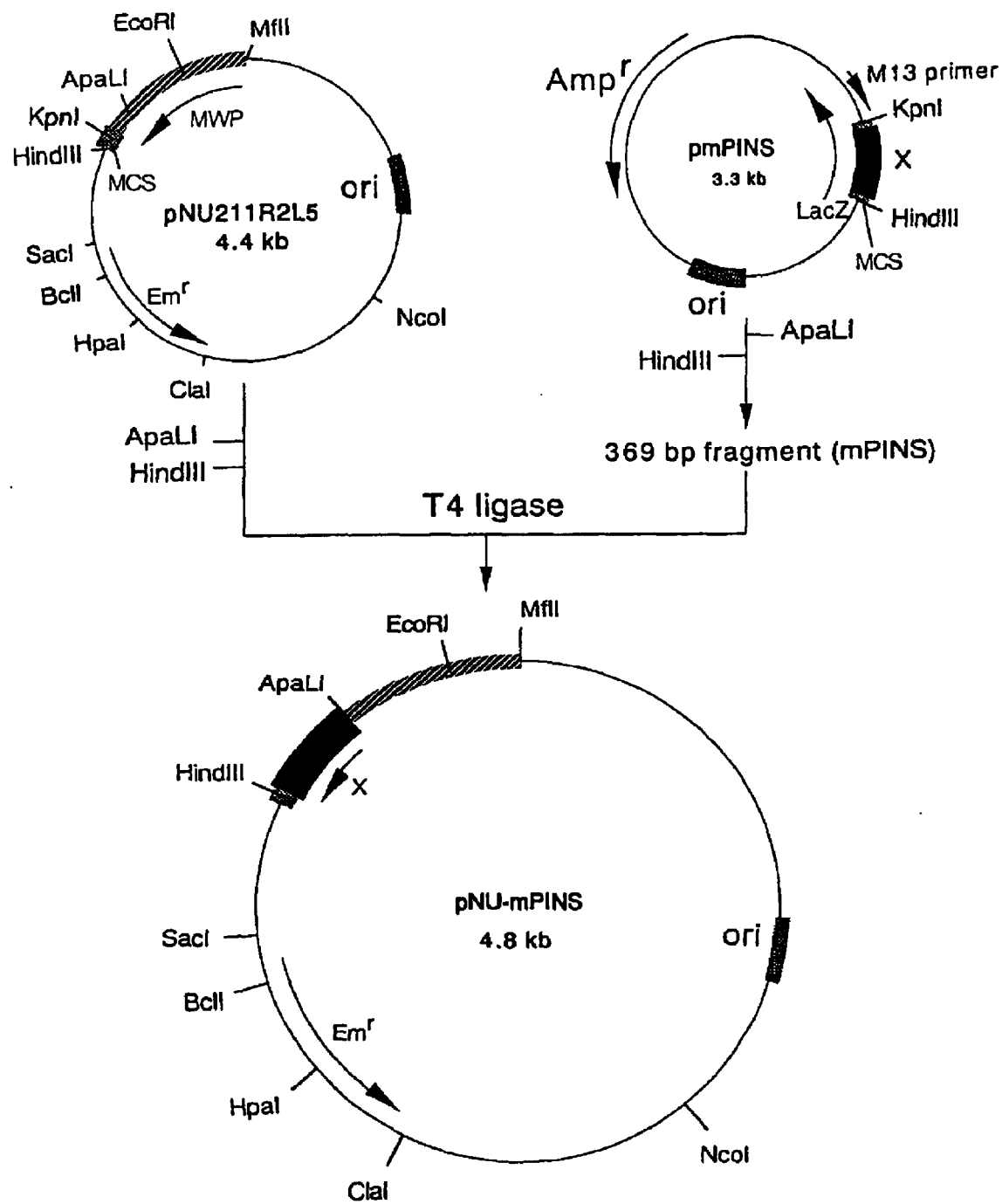
FIG. 3 is the schematic diagram depicting a process of introducing a fusion DNA into a *Bacillus brevis* expression vector (pNU211R2L5).

The present invention also provides a vector containing the DNA. The vector that can be used in the present invention is needed to have at least the following properties: it has an appropriate insertion site (i.e., a restriction site) to which the DNA of the present invention can be inserted; it can express the DNA in a host cell; and it is autonomously replicable in the host cell. The vector generally contains a promoter, in which the promoter is operably linked with the upstream of the DNA of interest. The vector may contain an origin of replication and a terminator sequence, and may also contain a selectable marker such as a drug resistance gene or an auxotrophy-complement gene. The vector of the present invention is preferably a plasmid which is replicable in a Bacillus bacterium. Examples of the plasmid include, but are not limited to, pNU200, pHY500 (Proc. Natl. Acad. Sci. USA, 86:3589–3593, 1989), pHY4831 (J. Bacteriol., 169:1239–1245, 1987), pNU100 (Appi. Microbiol. Biotechnol., 30:75–80, 1989), pNU211 (J. Biochem., 112:488–491, 1992), pNU211R2L5 (Japanese Patent Application Laid-open No. 7-170984), pHY700 (Japanese Patent Application Laid-open No. 4-278091), pHT210 (Japanese Patent Application laid-open No. 6-133782), pHT110R2L5 (Appl. Microbiol. Biotechnol., 42:358–363, 1994). According to an embodiment of the present invention, an expression vector pNU-mPINS can be prepared by the construction process as illustrated in FIG. 3.

The present invention also provides a host cell transformed with the vector as defined above. The host cell may be prokaryotic cells (e.g., bacteria) or prokaryotic cells (e.g., fungi, yeasts, animal cells, plant cells), and preferably a Bacillus bacterium. Examples of Bacillus bacterium as the host include, but are not limited to, *Bacillus brevis* strain 47 (FERM P-7224; JP-A- 60-58074 and JP-A-62-201589), strain 47K (JP-A- 2-257876), strain 31OK (JP-A- 6-296485) and strain HPD31 (FERM BP-1087; JP-A- 4-278091). The recombinant bacterium *Bacillus brevis* strain 47-5Q transformed with an expression vector pNU-mPINS has been deposited under the terms of the Budapest Treaty on Apr. 20, 1999 at the National Institute of Bioscience and Human-technology, Agency of Industrial Science and Technology, Japan (1–3, Higashi 1-chome, Tsukuba-shi, Ibaragi-ken, Japan) under the accession No. FERM BP-6706.

The expression vector prepared as mentioned above is then introduced into a competent host cell, preferably a Bacillus bacterium cell. The bacterium cell is cultured in a suitable culture medium under the conditions which allow the expression of the DNA to produce the recombinant fusion polypeptide of interest extracellularly or intracellularly, preferably extracellularly. The recombinant fusion polypeptide is then collected and purified The introduction of the expression vector into the host cell may be performed by any conventional method such as electroporation (Methods in Enzymol., 217:23–33, 1993). The purification of the fusion polypeptide may be performed by an appropriate combination of any conventional methods such as solvent extraction, ultrafiltration, ammonium sulfate fractionation, HPLC, gel filtration chromatography, ion exchange chromatography, affinity chromatography, hydrophobic interaction chromatography, electrophoresis and isoelectric focusing.

The fusion polypeptide may be treated with a protease and/or a peptidase which can cleave the fission polypeptide enzymatically, such as thrombin and carboxypeptidase B as used in the examples below, resulting in the production of insulin. As illustrated in FIG. 1, at first, thrombin cleaves between the leader peptide (Y) and the chain, between the B-chain and the linker and between the linker and the A chain under suitable conditions. Preferable conditions for the specific cleavage with thrombin are as follows: pH 7.5–8.5 (preferably with Tris buffer); temperature of 3–6° C., preferably 4° C.; the substrate:enzyme ratio=5:1 to 125:1 (molar ratio), more preferably 25:1; a time period of 1–24 hours. Next, carboxypeptidase B removes the Arg residue remaining at the C terminus of the B-chain, thus producing insulin (see FIG. 1). The enzymes may be used in amounts sufficient to cause the cleavage of the fusion protein.

According to the present invention, insulin can be obtained by culturing a transformed Bacillus bacterium prepared as described above to accumulate a fusion protein containing an insulin sequence outside the cell, and then cleaving the collected fusion protein.

The recombinant insulin prepared in this manner has the same amino acid sequence, disulfide bridges and biological activity as those of the naturally occurring insulin and, therefore, is useful as a therapeutic medicament for insulin-dependent diabetes mellitus.

EXAMPLES

The present invention will be illustrated in detail in the following examples. These examples, however, should not be construed to limit the scope of the invention.

In the preparation of a DNA encoding a fusion protein, a method was employed in which DNA fragments amplified by PCR reaction were ligated by a ligation reaction with a DNA ligase. In the specification, the term "MWPsp" means a MWP-derived signal peptide, the term "MWPmp9" means N-terminal 9 amino acid residues of the mature MWP.

EXAMPLE 1

Construction of Vector (pmPINS) Having MWPsp-MWPmp9-GSLQPR-Bchain-RGHRP-Linker-PR-Achain Fusion DNA Integrated Therein (1) Preparation of DNA fragment for MWPsp-MWPmp9
a Template DNA:
A genomic DNA extracted from *Bacillus brevis* strain 47–5Q by a known method (Molecular Cloning 2nd ed., A Laboratory Manual, Cold Spring Harbor Laboratory, 1989): 840 ng
b. Primers:
Forward primer: 5'-GTCGTFAACAGTGTATTGCT-3' (SEQ ID NO:7)
Reverse primer: 5'-AGCTGTAGTAGTTGCTGC-3' (SEQ ID NO:8)
These primers were chemically synthesized based on the nucleotide sequence of MWP determined by Yamagata, H. et al. (J. Bacteriol., 169:1239–1245, 1987) and Tsuboi, A. et al. (J. Bacteriol., 170:935–945, 1988) and added at the final concentration of 0.1 μM.
c. Taq DNA Polymerase:
A commercially available product (GIBCO BRL) (5U) was added.
d. Other materials:
Tris-HCl (final concentration: 20 mM, pH 8), MgCl$_2$ (final concentration: 2.5 mM), dNTPs (dATP, dGTP, dCTP, dTIP; final concentration: 50 μM for each) were added.

Materials "a" to "d" were mixed in a 0.5-ml tube so that the total volume of the reaction solution became 100 μl. PCR reaction was then performed according to a conventional manner (Innis, M. A. et al., PCR Protocols, A guide to methods and applications, Academic Press, 1990) under the conditions: denaturation temperature: 94° C.-1 min.; annealing temperature: 50° C.-1 min.; DNA chain elongation temperature: 72° C.-1 min.; for 30 cycles. After the PCR was completed, the reaction solution was concentrated with phenol, and then applied to a 0.8% agarose gel to perform electrophoresis under conventional conditions. The agarose gel was treated using Ultrafree C3H (Millipore) to collect a PCR product (i.e., a DNA fragment for MWPsp-MWPmp9) therefrom. The collected PCR product was extracted with phenol, precipitated with ethanol and then dried in vacuo. The dried product was dissolved in an appropriate volume of distilled water, and then subjected to blunting reaction using DNA blunting kit (Takara Shuzo Co., Ltd.) according to the instructions by the manufacturer.

(2) Preparation of DNA Fragment for Proinsulin
A blunt-ended DNA fragment for proinsulin was prepared in the same manner as mentioned in (1), except the following things.

As the template DNA, a plasmid vector having human preproinsulin DNA integrated therein (10 ng) was used. This recombinant plasmid vector was prepared in the following manner. Human pancreatic cDNA was synthesized from a commercially available human pancreatic mRNA (CLONTECH) using 1st strand cDNA synthesis kit (Pharmacia) according to the instructions by the manufacturer. PCR was performed using the CDNA as a template and a forward primer: 5'-ATGGCCCTGTGGATGCGCC-3' (SEQ ID NO:9) and a reverse primer: 5'-CTAGTTGCAGTAGTTCTCC-3' (SEQ ID NO:10) both synthesized based on the nucleotide sequence of human preproinsulin gene determined by Bell, G. I. et al. (Nature, 282:525–527, 1979) under the conditions: conditions: 94° C.-1 min.; 60° C.- 1 min.; 72° C.-1 min.; for 35 cycles. The PCR product, i.e., human preproinsulin DNA, was cloned into pGEM-T vector (Promega).

As the primers, a forward primer: 5'-TTTGTGAACCAACACCTG-3' (SEQ ID NO:11) and a reverse primer: 5'-CTAGTTGCAGTAGTTCTCC-3' (SEQ ID NO:10) were used.

The following PCR conditions were employed: denaturation temperature: 94° C.–1 min.; annealing temperature: 47° C.-1 min.; DNA chain elongation temperature: 72° C.-30 sec.; for 25 cycles).

(3) Preparation of DNA Fragment for GSLQPR-Bchain-R
A blunt-ended DNA fragment for GSLQPR-Bchain-R was prepared in the same manner as mentioned in (1), except the following things. The resulting DNA fragment was subjected to phosphorylation reaction using T4 polynucleotide kinase (Nippon Gene Co., Ltd.) according to the instructions by the manufacturer to prepare a phosphorylated DNA fragment for GSLQPR-Bchain-R.

As the template DNA, the proinsulin PCR product prepared in (2) (10 ng) was used.

As the primers, a forward primer: 5'-GGTTCCTTGCAACCTCGTTTGTGAACCAACACCTG-3' (SEQ ID NO:12) and a reverse primer: 5'-GCGGGTCTTGGGTGTGTA-3' (SEQ ID NO:13) were used.

The following PCR conditions were employed: denaturation temperature: 94° C.-1 min.; annealing temperature: 47° C.-1 min.; DNA chain elongation temperature: 72° C.-30 sec.; for 25 cycles).

(4) Preparation of DNA fragment for Linker

A blunt-ended DNA fragment for Linker was prepared in the same manner as mentioned in (1), except the following things.

As the template DNA, the proinsulin PCR product prepared in (2) (10 ng) was used.

As the primers, a forward primer: 5'-GAGGCAGAGGACCTGCAG-3' (SEQ ID NO:14) and a reverse primer: 5'-CTGCAGGGACCCCTCCAG-3' (SEQ ID NO:15) were used.

The following PCR conditions were employed: denaturation temperature: 94° C.-1 min.; annealing temperature: 55° C.-1 min.; DNA chain elongation temperature: 72° C.-30 sec.; for 25 cycles).

(5) Preparation of DNA Fragment for GHRP-Linker

A blunt-ended DNA fragment for GHRP-Linker was prepared in the same manner as mentioned in (4), except the following things. The resulting DNA fragment was subjected to phosphorylation reaction using T4 polynucleotide kinase (Nippon Gene Co., Ltd.) according to the instructions by the manufacturer to prepare a phosphorylated DNA fragment for GHRP-Linker.

As the template DNA,, the PCR product (the DNA fragment for Linker) prepared in (4) (10 ng) was used.

As the forward primer, a primer: 5'-GGTCACCGTCCAGAGGCAGAGGACCTGCAGGTGGGG-3' (SEQ ID NO:16) was used.

The following PCR conditions were employed: denaturation temperature: 94° C.-1 min.; annealing temperature: 55° C.-1 min.; DNA chain elongation temperature: 72° C.-30 sec.; for 25 cycles).

(6) Preparation of DNA Fragment for Achain

A blunt-ended DNA fragment for Achain was prepared in the same manner as mentioned in (1), except the following things.

As the template DNA,, the PCR product for proinsulin prepared in (2) (10 ng) was used.

As the primers, a forward primer: 5'-GGCATTGTGGAACAATGCTGT-3' (SEQ ID NO:17) and a reverse primer: 5'-CTAGTTGCAGTAG1TCTCCAGCTGGTA-3' (SEQ ID NO: 18) were used.

The following PCR conditions were employed: denaturation temperature: 94° C.-1 min.; annealing temperature: 55° C.-1 min.; DNA chain elongation temperature: 72° C.-30 sec.; for 25 cycles).

(7) Preparation of DNA Fragment for PR-Achain

A bluntended DNA fragment for PR-Achain was prepared in the same manner as mentioned in (6), except the following things. The resulting DNA fragment was subjected to phosphorylation reaction using T4 polynucleotide kinase (Nippon Gene Co., Ltd.) according to the instructions by the manufacturer to prepare a phosphorylated DNA fragment for PR-Achain.

As the template DNA,, the PCR product (i.e., the DNA fragment for Achain) prepared in (6) (10 ng) was used.

As the forward primer, a primer: 5'-CCACGTGGCATTGTGGAACAATGCTGT-3' (SEQ ID NO: 19) was used.

The following PCR conditions were employed: denaturation temperature: 94° C.-1 min.; annealing temperature: 55° C.-1 min.; DNA chain elongation temperature: 72° C.-30 sec.; for 25 cycles).

(8) Preparation of Fusion DNA for MWPsp-MWPmp9-GSLQPR-Bchain-R

A blunt-ended fusion DNA fragment for MWPsp-MWPmp9-GSLQPR-Bchain-R was prepared in the same manner as mentioned in (1), except the following things.

As the template DNA,, a product prepared by mixing appropriate amounts of the DNA fragment for MWPsp-MWPmp9 prepared in (1) and the DNA fragment for GSLQPR-Bchain-R prepared in (3) and reacting the mixture using a DNA ligation kit (Takara Shuzo Co., Ltd.) at 16° C. for 30 minutes was used.

As the reverse primer, a primer: 5'-GCGGGTCTTGGGTGTGTA-3' (SEQ ID NO:13) was used.

The following PCR conditions were employed: denaturation temperature: 94° C.-1 min.; annealing temperature: 47° C.-1 min.; DNA chain elongation temperature: 72° C.-30 sec.; for 25 cycles).

The PCR product was phosphorylated using T4 polynucleotide kinase (Nippon Gene Co., Ltd.) according to the instructions by the manufacturer. The phosphorylated PCR product was digested with Hinc 11 using a DNA ligation kit (Takara Shuzo Co., Ltd.) and integrated into a vector (STRATAGENE, Blue Script SK-). E. coli strain DH5α was transformed with the vector according to a known method (Molecular Cloning 2nd ed., A Laboratory Manual, Cold Spring Harbor Laboratory, 1989), and the vector (i.e., the plasmid DNA) was then isolated from the transformant. The plasmid DNA was sequenced using a forward primer (M13 forward primer) or a reverse primer (M13 reverse primer) to confirm the presence of the fusion DNA for MWPsp-MWPmp9-GSLQPR-Bchain-R. The second round PCR was performed using a vector having the fusion DNA for MWPsp-MWPmp9-GSLQPR-Bchain-R integrated therein as a template DNA and a forward primer: 5'-GTCGTTAACAGTGTATTGCT-3' (SEQ ID NO:7) and a reverse primer: 5'-GCGGGTCTTGGGTGTGTA-3' (SEQ ID NO: 13) in the same manner as mentioned above, thereby producing a blunt-ended fusion DNA for MWPsp-MWPmp9-GSLQPR-Bchain-R.

(9) Preparation of Fusion DNA for MWPs-MWPmp9-GSLQPR-Bchain-RGHRP-Linker

A blunt-ended fusion DNA for MWPsp-MWPmp9-GSLQPR-Bchain-RGHRP-Linker was prepared in the same manner as mentioned in (g), except the following things.

As the template DNA, for the first round PCR, a product prepared by mixing appropriate amounts of the fusion DNA for MWPspMWPmp9-GSLQPR-Bchain-R prepared in (8) and the DNA fragment for GHRP-Linker prepared in (5) and then reacting the mixture using a DNA ligation kit (Takara Shuzo Co., Ltd.) at 16° C. for 30 minutes was used.

As the reverse primer, a primer: 5'-CTGCAGGGACCCCTCCAG-3' (SEQ ID NO:15) was used.

(10) Preparation of a Vector Having Fusion DNA for MWPsp-MWPmp9-GSLQPR-Bchain-RGHRP-Linker-PR-Achain Integrated Therein A vector having a fusion DNA for MWPsp-MWPmp9-GSLQPR-Bchain-RGHRP-Linker-PR-Achain integrated therein (pmPINS) was prepared in the same manner as mentioned in (8), except the following things.

As the template DNA, for the first round PCR, a product prepared by mixing appropriate amounts of the fusion DNA for MWPsp-MWPmp9-GSLQPR-Bchain-RGHRP-Linker prepared in (9) and the DNA fragment for PR-Achain prepared in (7) and then reacting the mixture using a DNA ligation kit (Takara Shuzo Co., Ltd.) at 16° C. for 30 minutes was used.

As the reverse primer for the first round PCR, a primer: 5'-CTAGTTGCAGTAGTTCTCCAGCTGGTA-3' (SEQ ID NO: 18) was used.

The following PCR conditions were employed: denaturation temperature: 94° C.-1 min.; annealing temperature: 50° C.-1 min.; DNA chain elongation temperature: 72° C.-1 min.; for 25 cycles).

EXAMPLE 2

Figure 2:
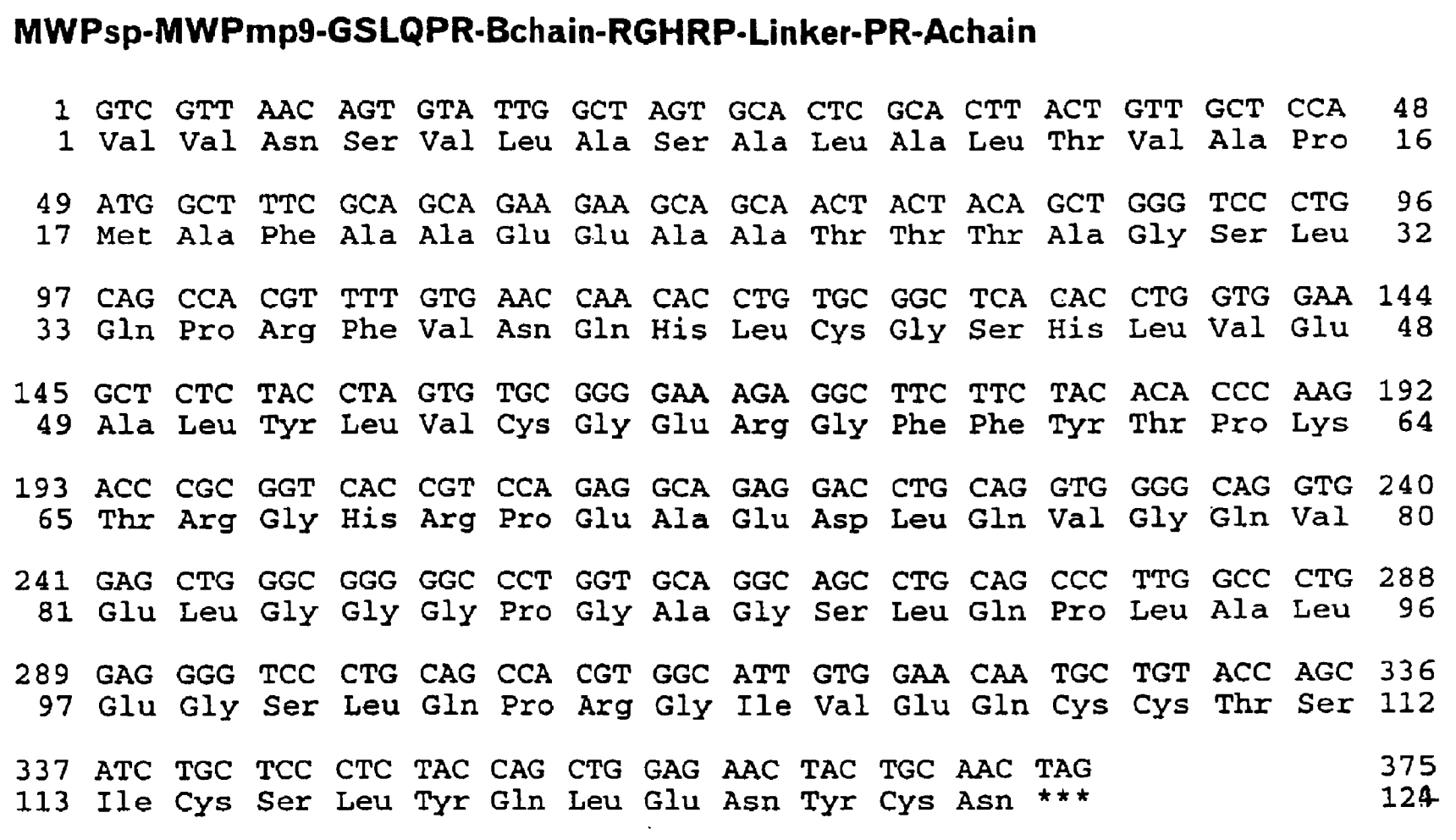

Expression and Secretion of Fusion DNA (1) Nucleotide Sequence of Fusion DNA and Amino Acid Sequence of Fusion Protein Encoded by the fusion DNA The nucleotide sequence of the fusion DNA prepared in Example 1 and the amino acid sequence of a fusion protein encoded by the fusion DNA are shown in FIG. 2.

(2) Expression and Secretion of Fusion DNA

The expression of a fusion protein encoded by the fusion DNA prepared in Example 1 was performed. The fusion DNA was integrated into an expression vector as illustrated in FIG. 3.

Specifically, the vector pmPINS into which the fusion DNA was integrated was digested with ApaL I and Hind III. The digestion product was subjected to electrophoresis on a 0.8% agarose gel, and a gel portion containing the fusion DNA was excised. Appropriate amounts of the excised fusion DNA and an expression vector for *Bacillus brevis* (pNU211R2L5; JP-A-7-170984) which had been digested with ApaL I and Hind III were mixed, and the mixture was reacted using a DNA ligation kit (Takara Shuzo Co., Ltd.) at 16° C. for 30 minutes, thereby the fusion DNA was integrated into the expression vector. Thus, an expression vector pNU-mPINS having the fusion DNA integrated therein was prepared. *Bacillus brevis* strain 47-5 (FERM BP-1664) was transformed with the expression vector according to a known method (Methods in Enzymol., 217:23–33, 1993), and then plated on T2 agar culture medium [polypeptone (1%), meat extract (0.5%), yeast extract (0.2%), uracil (0.1 mg/ml), glucose (1%), erythromycin (10 μg/ml), agar (1.5%); pH 7] to collect the transformants.

The transformants were cultured in T2 culture medium (a medium having the same composition as T2 agar culture medium except that agar was eliminated) at 37° C. for 1 day, and plasmid DNA was isolated therefrom by a known method (Molecular Cloning 2nd ed., A Laboratory Manual, Cold Spring Harbor Laboratory, 1989). The plasmid DNA was treated with ApaL I and Hind III to confirm the presence of the fusion DNA integrated therein. With respect to the transformant that had been confirmed the presence of the fusion DNA integrated therein, expression and secretion of a fusion protein encoded by the integrated fusion DNA were performed. A cell suspension which had been cultured in T2 culture medium at 37° C. for 1 days was added to a culture medium [polypeptone (3%), yeast extract (0.4%), glucose (3%), MgSO$_4$.7H$_2$O (0.01%), MnSO$_4$. 4H$_2$O (0.001%), erythromycin ( 10 μg/ml); pH 8] at a ratio of 1/1000 (by volume), and then cultured with shaking at 30° C. for 4 days.

Figure 4:
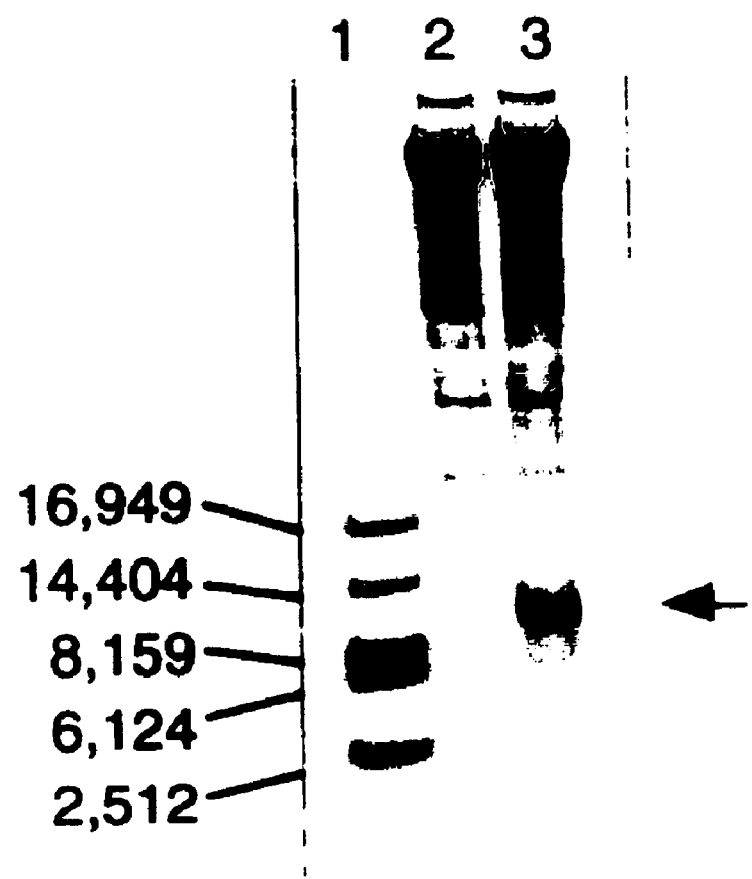
FIG. 4 is the photograph of the electrophoresis of the media after culture of transformants: lane 1, a marker peptide; lane 2, a negative control (i.e., a transformant with only plasmid pNU211R2L5 and without a foreign protein); and lane 3, a transformant MWPmp9-GSLQPR-Bchain-RGHRP-Linker-PR-Achain.

After the cultivation, the culture medium was centrifuged at 15,000 rpm for 2 min. to give a culture supernatant. The culture supernatant was subjected to electrophoretic protein analysis by a known method (Laemmli, U. K., Nature, 227:680–685, 1970). That is, the culture supernatant (18 μl) was added with buffer 1 [125 mM Tris-HCl (pH 6.8), 20% glycerol, 4% SDS, 10% 2-mercaptoethanol] (2 μl), and the mixed solution was boiled for 5 min. The mixed solution was added with buffer 2 [250 mM Tris-KCl (pH 6.5), 50% glycerol, 0.5% BPB] (4 μl). The resulting mixed solution was electrophoresed on a 15/25% SDS polyacrylamide gel (DAIICHI PURE CHEMICALS, Co., Ltd.) (electrophoresis buffer: 100 mM Tris, 100 mM Tricine, 0.1% SDS). After the electrophoresis, the gel was subjected to Coomassie staining to determine the presence of the expression and secretion of the fusion protein. As shown in FIG. 4, for the culture medium of the cells transformed with pNU-mPINS containing the fusion DNA, a band (marked with an arrow) corresponding to the fusion protein was detected (lane 3); whereas for the culture medium of the cells having the vector without the fusion DNA, such a band was not detected (lane 2).

EXAMPLE 3

Figure 5:
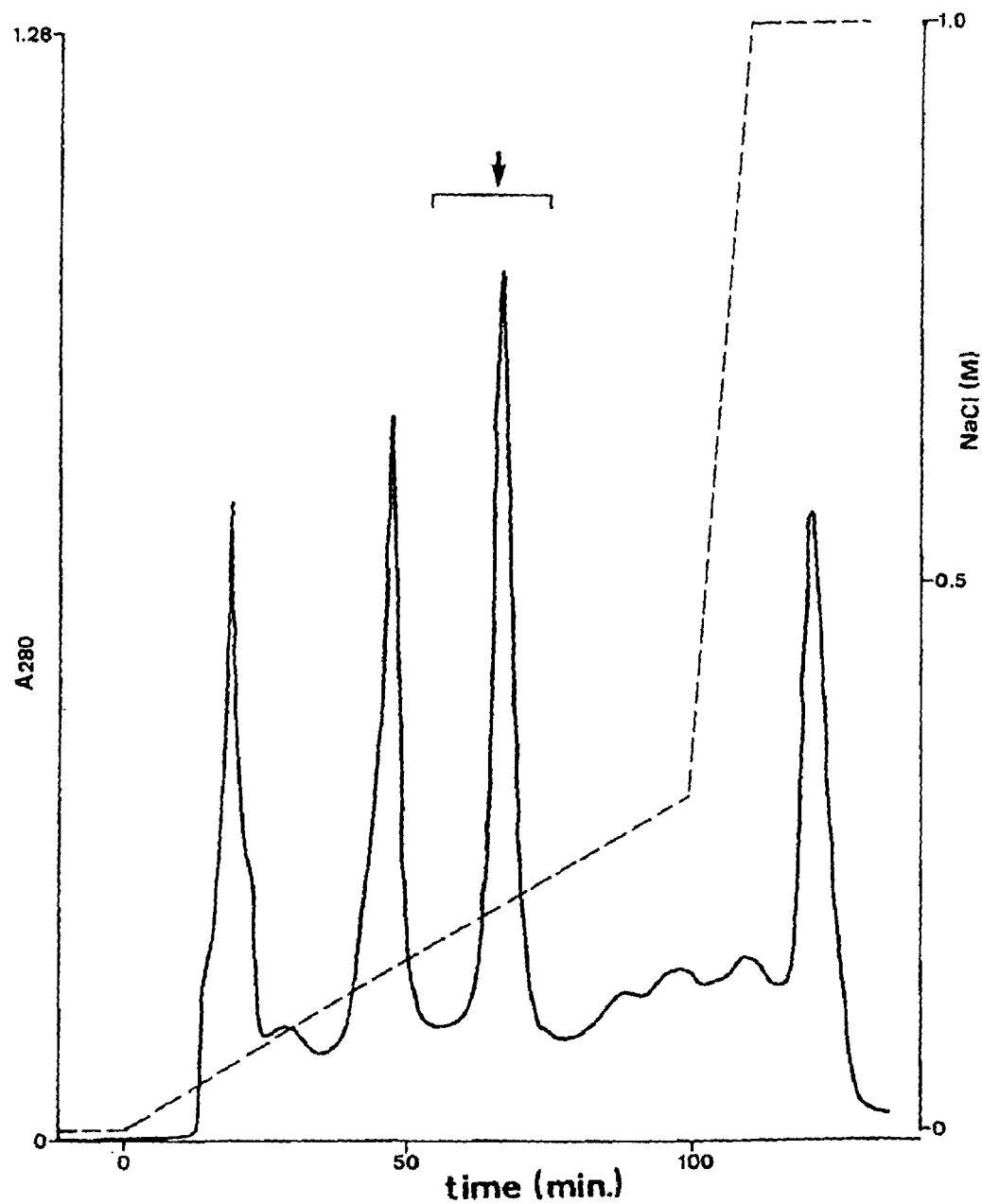
FIG. 5 shows the chromatogram of the fusion protein MWPmp9-GSLQPR-Bchain-RGHRP-Linker-PR-Achain isolated and purified by XL chromatography.
Figure 6:
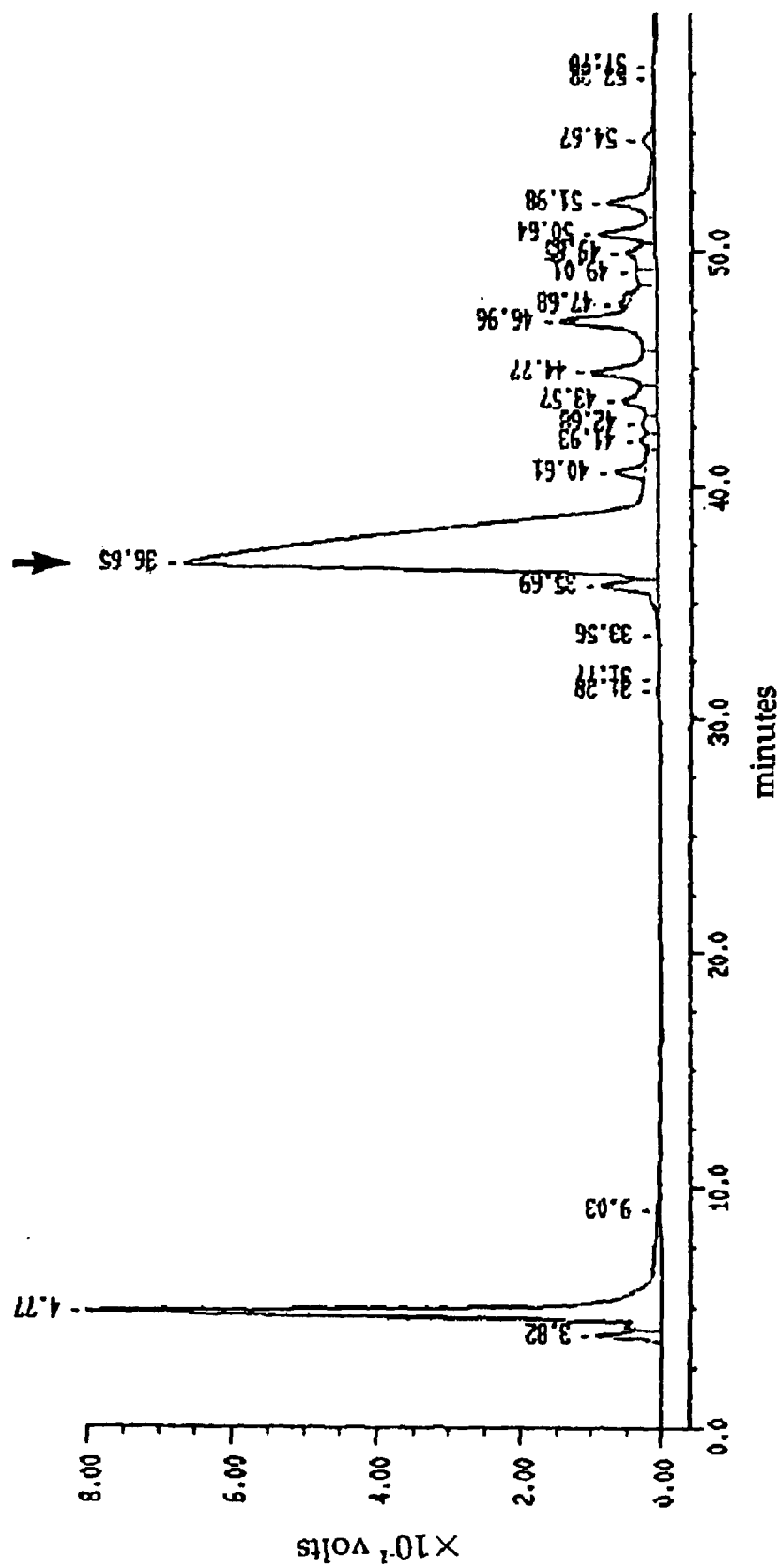
FIG. 6 shows the chromatogram of the fusion protein MWPmp9-GSLQPR-Bchain-RGHRP-Linker-PR-Achain isolated and purified by HPLC.

Conversion into Insulin (I) Isolation and Purification of Fusion Protein, MWPmp9-GSLQPR-Bchain-RGHRP-Linker-PR-Achain Cells transformed with pNU-mPINS was cultured at 37° C. for 1 day. An aliquot (50 μl) of the cell suspension was added to a culture medium [polypeptone (3%), yeast extract (0.4%), glucose (3%), MgSO$_4$.7H$_2$O (0.01%), MnSO$_4$.4H2O (0.001%), erythromycin (10 μg/ml); pH g (50 ml) The mixed culture medium was charged dividedly into six 500-ml conical flasks, and then cultured with shaking at 30° C. for 4 days. The culture medium was centrifuged at 9,000 tpm for 20 min. The supernatant was dialyzed against a buffer [20 mM Na—PO$_4$, 150 mM, pH 8] at 4° C., and then centrifuged at 10,000 rpm for 20 min. The supematant was applied to a Ni-chelating column (Pharmacia; 5×10 cm) to elute the fusion protein of interest with the buffer supplemented with 60 mM imidazole. The elution fraction was added with EDTA and benzamidine (1 mM each) and kept at 4° C. Thereafter, urea (final concentration: 1 M) and cystein (final concentration: 1 mg/ml) were fluther added to the elution fraction. The mixed solution was adjusted to pH 10.8 with 1N NaOH and stirred at the same temperature for 1 hour. The solution was dialyzed against a buffer [20 mM Tris, 1 mM EDTA; pH 8.0]. The dialysate was added with urea (final concentration: 1 M) and 2-propanol (final concentration: 20%) and then applied to Q-Sepharose XL column (Pharmacia; 1.6×10 cm). The column was sufficiently equilibrated with a buffer [20 mM Tris, 1mM EDTA, 1 M urea, 20% 2-propanol; pH 8] and then eluted with the buffer supplemented under gradient with 1 M NaCl. In FIG. 5, the elution pattern is shown. The elution fractions eluted with 160 mM–200 mM NaCl (shown by the arrow) were combined, and adjusted to pH 3 with 1N HCl. The solution was concentrated using an ultrafilter (fractionation molecular weight: 3,000), and then applied to Vydac214TP54 (CYPRESS; C4 column, 4.6×250 rnm) for purification by HPLC. The column was equilibrated with 25% acetonitrile and 0.1% TFE solution, and then eluted under gradient with 33% acetonitrile and 0.1% TFE solution. In FIG. 6, the elution pattern is shown. The fractions eluted with 30–31% acetonitrile (shown by the arrow) were centrifuged and concentrated to dryness. The resulting product was used in the subsequent cleavage experiment.

(2) Conversion Into Insulin and Purification Thereof

The fusion protein prepared in (1) as a dry product, MWPmp9-GSLQPR-Bchain-RGHRP-Linker-PR-Achain, was dissolved in a appropriate amount of 0.1% TFA, and then added with 0.1 M Tris buffer (pH 8) to the final concentration of 20 nmol/ml. The resulting solution was cooled to 4° C., and then added with a thrombin solution (250 μmol/ml) at the substrate:enzyme ratio of 25:1 (molar base). After 9 hours, a appropriate amount of 10% TFA was added to the reaction solution to adjust to pH 2, thereby terminating the reaction. The thrombin used was thrombin of JP grade (ITOHAM FOODS INC.) which had been re-purified using Macro Prep CM (Bio Rad) and Lysine Sepharose 4B (Pharmacia).

To isolate insulin-Arg, which had an Arg residue at the C terminus of the B chain cleaved with thrombin, by reversed phase HPLC, the reaction-terminated solution after the thrombin treatment was applied to Mightysil RP4 column (Cica-MERCK; 20×250 mm), the column was equilibrated with 25% acetonitrile and 0.1% TFA solution and then eluted under gradient with 35% acetonitrile and 0.1% TFA solution. The fractions eluted with 30–31% acetonitrile were centrifuged and concentrated to dryness. The resulting dry product was used in the subsequent experiment.

The dry product insulin-Arg was dissolved in a appropriate amount of 0.1% TFA and then added with 0.1M Tris buffer (pH 8) to the final concentration of 1 mg/mi. The resulting solution was added with a carboxypeptidase B solution (Sigma; 4.7 mg/ml) at the substrate:enzyme ratio of 500:1 (molar base), and the reaction solution was allowed to react at 25° C. for 12 hours. The reaction solution was added with a appropriate amount of 10% TFA to adjust to pH 2, thereby terminating the reaction. To isolate insulin from the reaction-terminated solution, the reversed phase HPLC was performed in the same manner as mentioned for the isolation of the insulin-Arg. (3) Amino Acid Analysis of Insulin At first, the total amino acid of the insulin was analyzed. The insulin obtained in (2) (about 2 nmoles) was added with 6N HCl (200 μl) and 5% phenol (20 μl). The resulting reaction solution was deaerated and the tube containing the reaction solution was sealed. The reaction solution was allowed to react at 110° C. for 24 hours to cause hydrolysis reaction, and then dried. The resulting dry product was dissolved in 0.01N HCl (100 μl) and filtrated on a 0.2-μm filter. An aliquot (50 μl) of the filtrate was analyzed using Hitachi amino acid analyzer Model L-8500 (HITACHI, Ltd.).

Next, the cysteic acid content of the insulin was analyzed. The insulin obtained in (2) (about 2 nmoles) was dissolved in a formic acid/methanol (5:1) mixed solution (40 μl), and cooled to −20° C. The cooled solution was added with a 99% formic acid/30% aqueous hydrogen peroxide (19:1) mixed solution (400 μl) which had been cooled to −20° C., and then allowed to react at −20° C. for 4 hours. After the reaction was completed, distilled water (3 ml) was added to the reaction solution and lyophilized. The resulting dry product was hydrolyzed in the same manner as mentioned above, and then analyzed.

The analytical values for Val determined in the total amino acid analysis and the cysteic acid analysis were compared, and the analytical value for cysteic acid was converted into the analytical value for cysteine of the total amino acid analysis. As shown in Table 1, the amino acid ratio of the insulin of the present invention was almost consistent with that of the naturally occurring insulin.

TABLE 1

| | INS analysis | | | | | |
|---|---|---|---|---|---|---|
| | Analytical | | | | INS calculated value | |
| Amino acid | value nmole | mol % | Number of residue | Residue nmole | Number of Residue | mol % |
| Cys-SO3H | 5.697 | 12.63% | 6.41 | 0.950 | | |
| Asp | 2.726 | 6.12% | 3.11 | 0.921 | 3 | 5.88% |
| Thr | 2.696 | 5.97% | 3.03 | 0.899 | 3 | 5.88% |
| Ser | 2.437 | 5.40% | 2.74 | 0.812 | 3 | 5.88% |
| Glu | 6.271 | 13.90% | 7.05 | 0.895 | 7 | 13.73% |
| Pro | 0.985 | 2.18% | 1.11 | 0.985 | 1 | 1.96% |
| Gly | 3.392 | 7.52% | 3.81 | 0.848 | 4 | 7.84% |
| Ala | 1.000 | 2.22% | 1.12 | 1.000 | 1 | 1.96% |
| Cys1/2 | | | | | 6 | 11.76% |
| Val* | 3.205 | 7.10% | 3.60 | 0.801 | 4 | 7.84% |
| Met | | | | | | |
| Ile | 1.409 | 3.12% | 1.58 | 0.705 | 2 | 3.92% |
| Leu | 5.462 | 12.10% | 6.14 | 0.910 | 6 | 11.76% |
| Tyr | 3.507 | 7.77% | 3.94 | 0.877 | 4 | 7.84% |
| Phe | 2.640 | 5.85% | 2.97 | 0.880 | 3 | 5.88% |
| Lys | 0.913 | 2.02% | 1.03 | 0.913 | 1 | 1.96% |
| His | 1.822 | 4.04% | 2.05 | 0.911 | 2 | 3.92% |
| Trp | | | | | | |
| Arg | 0.924 | 2.05% | 1.04 | 0.924 | 1 | 1.96% |
| | 45.122 | 100.00% | 50.73 | 0.889 | 51 | 100.00% |

(4) Peptide Mapping of Insulin

Figure 7:
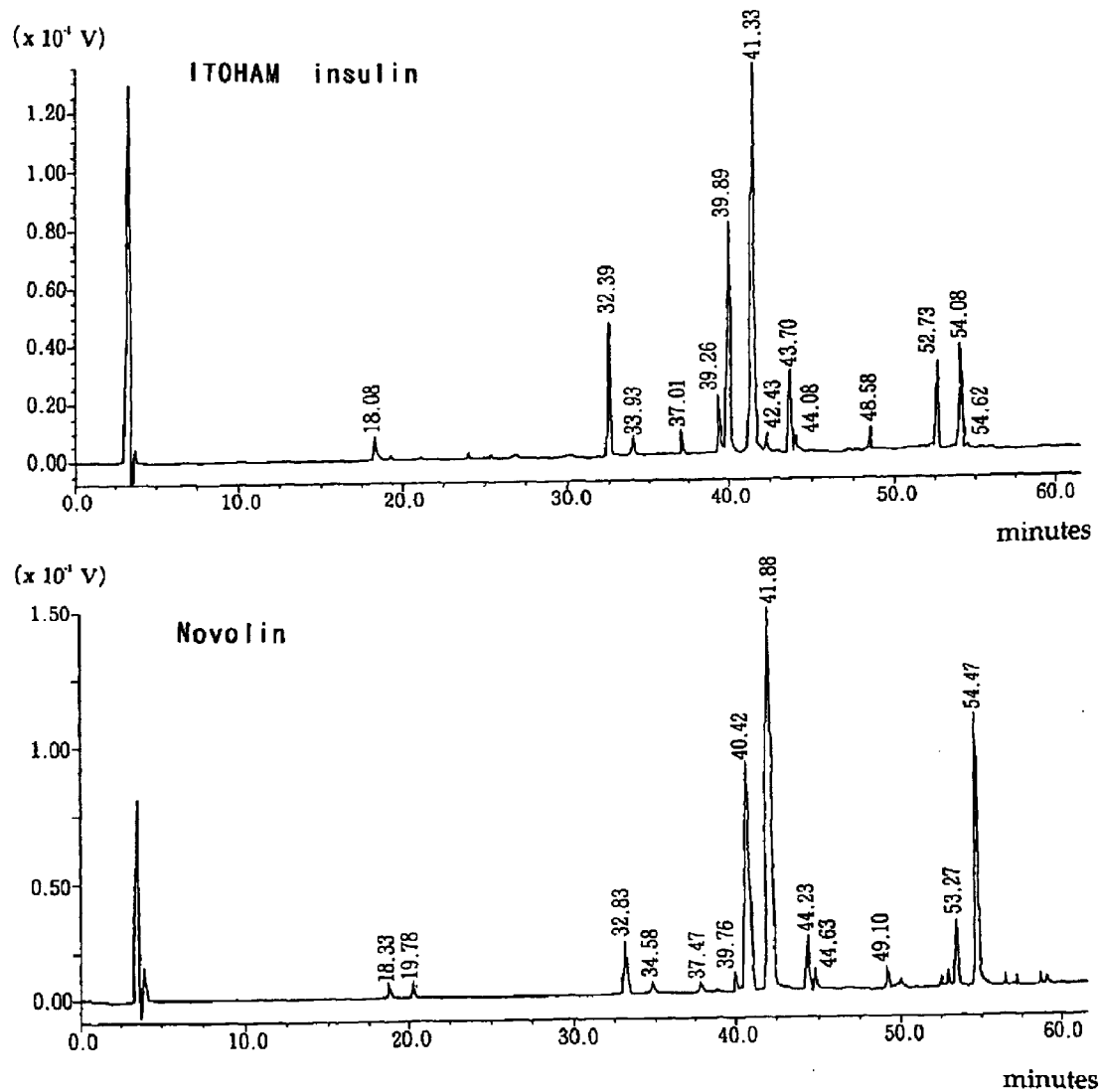
FIG. 7 shows the peptide mapping of ITOHAM insulin (the present invention) and Novolin Novolin 40, which is a commercially available insulin, sold by Novo Nordisk Pharma).

The insulin obtained in (2) (hereinafter, referred to as "ITOHAM insulin") and a commercially available insulin, Novolin 40, (Novo Nordisk Pharma)(hereinafter, referred to as "Novolin") (5 nmoles each) were separately dissolved in 0.81 M ammonium hydrogen carbonate (50 μl)and 2 mM EDTA solution (pH 7.8; 50 μl). The resulting solution was added with an aqueous V8 protease solution (Wako Pure Chemical Industries, Ltd.; 2 μml) (1.35 .92). The reaction solution was allowed to react at 25° C. for 24 hours, and 1% TFA solution was added thereto to adjust to pH 2, thereby terminating the reaction. The reaction-terminated solution was applied to Vydac218TP54 column (4.6×250 mm; C18 column), equilibrated with 5% acetonitrile and 0.1% TFA solution, and then eluted under gradient with 35% acetonitrile and 0.1% TFA solution. In FIG. 7, the elution pattern is shown. ITOHAM insulin and Novolin showed similar elution patterns to each other. Therefore, it is concluded that the both kinds of insulin have the similar disulfide bridging forms.

EXAMPLE 4

Biological Activity of Insulin

Figure 8:
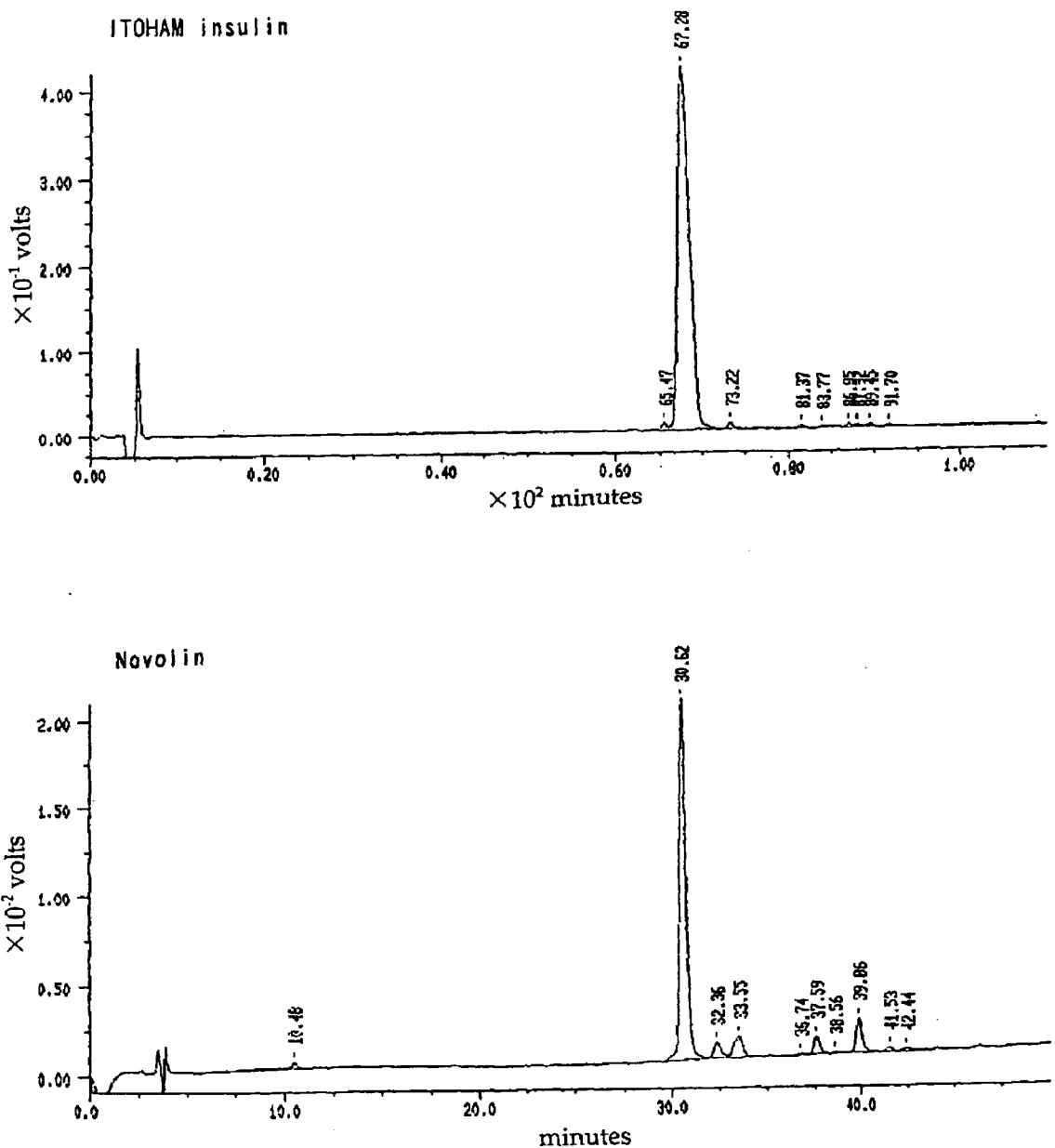
FIG. 8 shows the elution patterns of ITOHAM insulin (the present invention) and Novolin.

Novolin (1.2 ml) was treated with the same manner as in Example 3 (2) using Wakocil-II 5C18 AR Prep (Wako Pure Chemical Industries, Ltd.; 20×250 mm) to give insulin fractions. The insulin fractions of ITOHAM insulin obtained in Example 3 (2) and the insulin fractions of Novolin were analyzed using Vydac218TP54 (4.6×250 mm; C18 column). For each insulin sample, an aliquot was taken from the fractions so that the insulin contents for both kinds of insulin calculated based on the main peak areas became same, and then dried. As shown in FIG. 8, the elution pattern of Novolin had sub-peaks which were assumed to indicate the presence of polymeric materials. The subpeak level (i.e., total sub-peak area) of Novolin was 1.23 times greater than that of IHOHAM insulin.

ITOHAM insulin and Novolin thus obtained were separately dissolved in a solution containing 0.1% BSA, 0.9%

Figure 9:
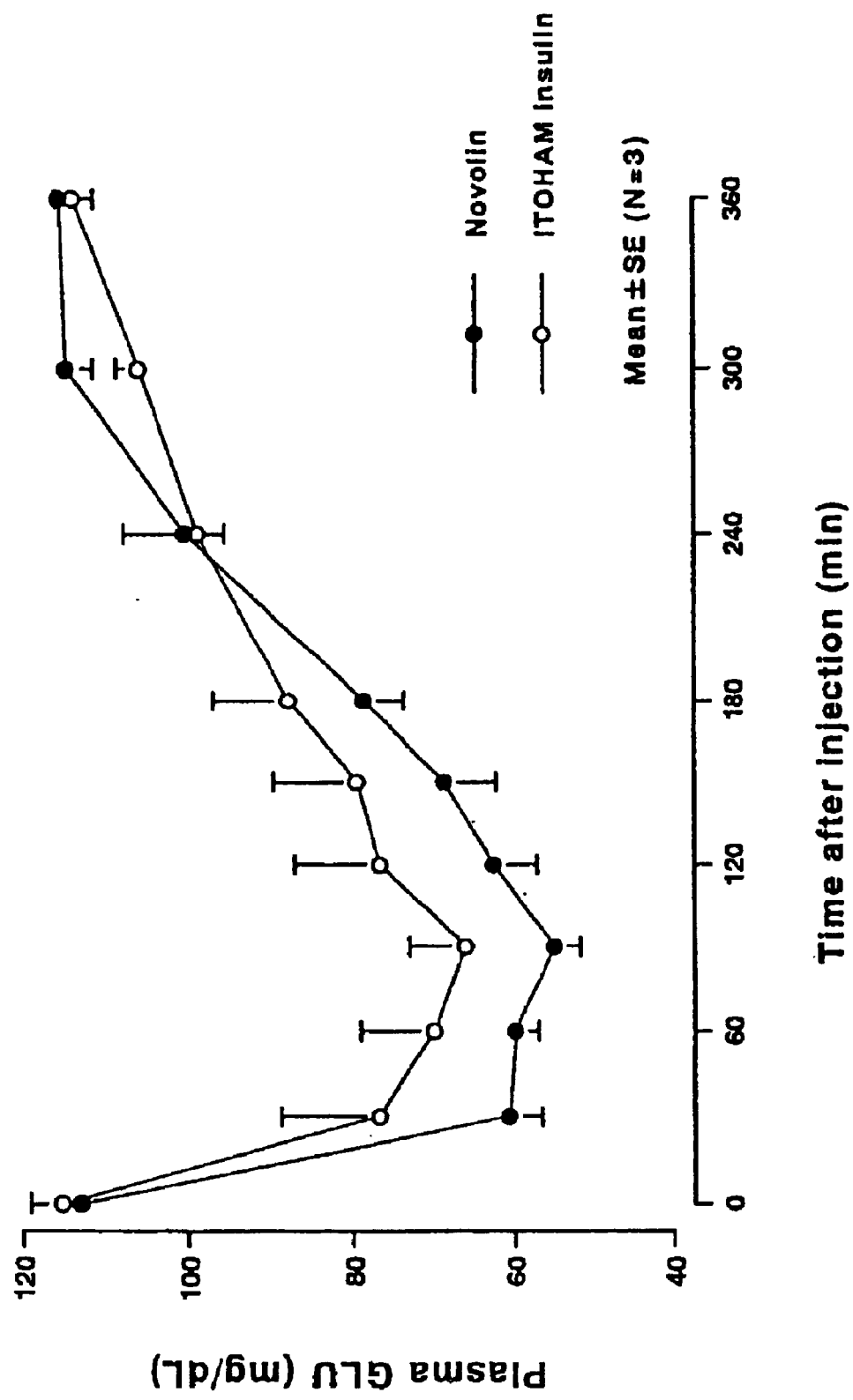
FIG. 9 shows the time courses of the plasma glucose levels after administration of ITOHAM insulin (the present invention) and Novolin.
Figure 10:
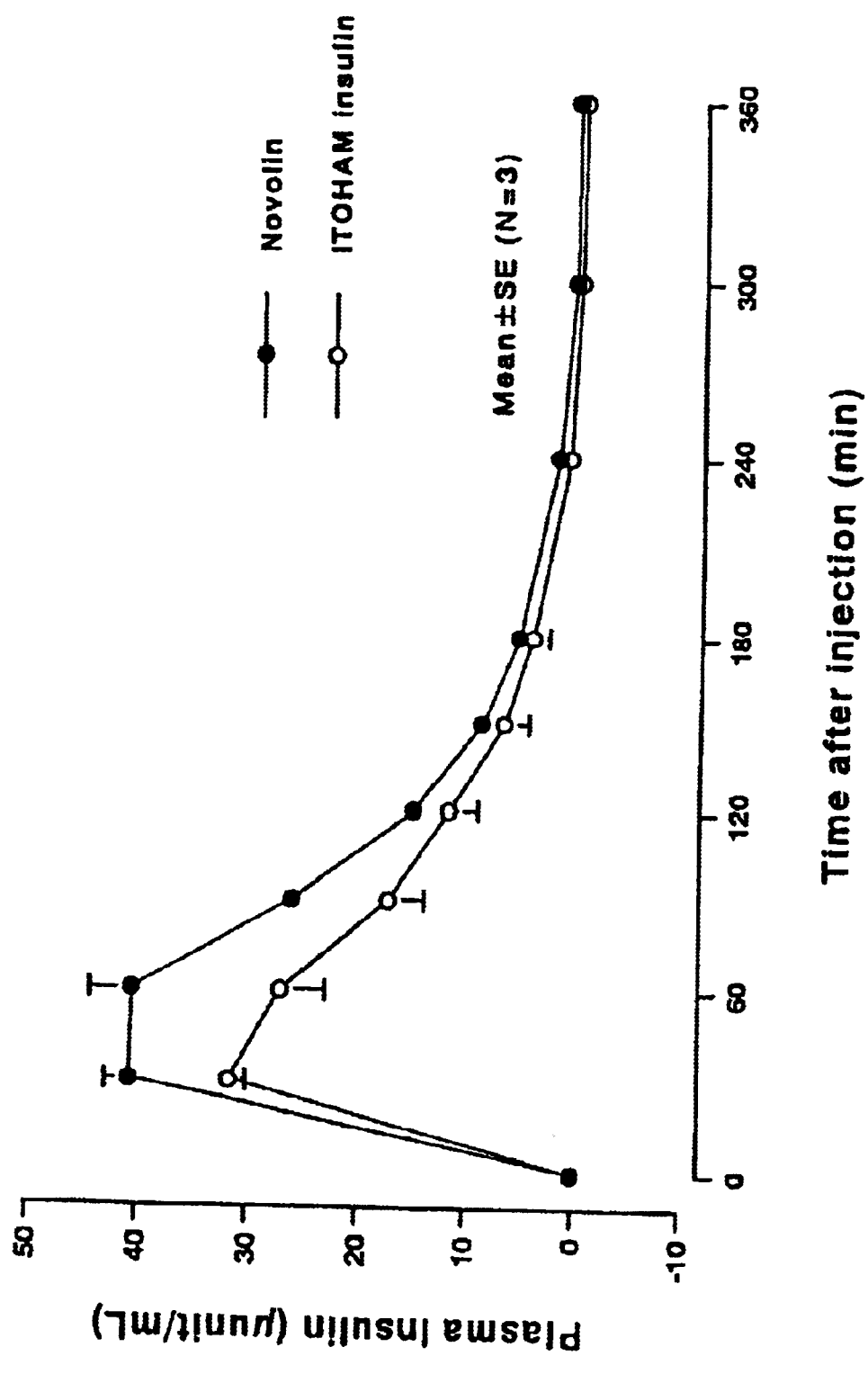
FIG. 10 shows the time courses of the plasma insulin levels after administration of ITOHAM insulin (the present invention) and Novolin.

NaCl and 0.1% phenol solution at the final concentration of 1 unit/ml (calculated based on the assumption that each insulin was 26 units/mg). The resulting solution (0.5 ml) was subcutaneously injected to the back of a Japanese Wister rabbit (Kbs:JW, 20.–2.5 kg). After the injection, blood was collected from the anterior auricular vein of the rabbit over a period of time. Each blood sample (0.45 ml) was added with a mix of glycolysis-inhibiting agents (NaF: 12.5 mg/ml, heparin-Na: 125 units/ml, EDTA-2Na: 48 mg/ml) (0.05 nm]) and fully mixed. The mixed solution was centrifuged at 3,000 rpm for 15 min. at 5° C., and the supernatant was used as a plasma sample. For each plasma sample, the plasma glucose level was determined using a biochemical automated analyzer (CIBA-CORNING; Express PLUS), and the plasma insulin level was determined using EIA kit (Wako Pure Chemical Industries, Ltd.). The time course of the plasma glucose level and the time course of the plasma insulin level are shown in FIG. 9 and FIG. 10, respectively. Both ITOHAM insulin and Novolin showed the decrease in plasma glucose level after the injection of insulin, demonstrating that both kinds of insulin acted to lower blood sugar. With respect to the plasma insulin level, both kinds of insulin showed the similar courses. The slight lower plasma glucose level and the slight higher plasma insulin level of Novolin than those of ITOHAM insulin are considered to be resulted from the increment of the sub-peaks in Novolin which were confirmed by the analysis by HPLC above.

As mentioned above, according to the present invention, a novel fusion protein convertible into insulin can be expressed and secreted in a high level in a Bacillus expression system. By treating the fusion protein of the present invention with thrombin and carboxypeptidase B, insulin having the same amino acid composition and biological activity as naturally occurring insulin can be obtained.

What is claimed is:

1. A DNA encoding a fusion protein of formula (I):

[Y]-[X1]-[B-chain]-[X2]-[Linker]-[X3]-[A-chain]   (I)

wherein

Y is a leader peptide sequence for expression and secretion of the protein, comprising the N-terminal 9 amino acid residues of the middle wall protein (MWP) which is one of the cell wall proteins (CWPs) from a bacterium belonging to the genus Bacillus;

X1 is an amino acid sequence which is cleavable with thrombin;

B-chain is the amino acid sequence of insulin B chain;

X2 is an amino acid sequence which is cleavable with thrombin

Linker is a linker sequence comprising at least one amino acid residue;

X3 is an amino acid sequence which is cleavable with thrombin; and

A-chain is the amino acid sequence of insulin A chain, and wherein the Y, X1, B-chain, X2, Linker, X3 and A-chain are ligated in the order indicated in formula (1).

2. The DNA of claim 1, wherein the amino acid sequences X1, X2 and or X3, which are used for enzymatic cleavage of a fusion protein, consist of the following sequences:

X1=GlySerLeuGlnProArg (SEQ ID NO:1);

X2=ArgGlyHisArgPro (SEQ ID NO:2); and

X3=ProArg.

3. The DNA of claim 1, wherein the linker sequence comprises the following amino acid sequence:

GluAlaGluAspLeuGlnValGlyGln-
ValGluLeuGlyGlyGlyProGlyAlaGly
SerLeuGlnProLeuAlaLeuGluGlySerLeuGln (SEQ ID NO:3).

4. The DNA of claim 1, wherein the DNA comprises a CWP signal peptide attached at the 5' end of the DNA.

5. A DNA comprising a nucleotide sequence encoding an amino acid sequence shown in SEQ ID NO:21.

6. The DNA of claim 5, wherein the DNA comprises a nucleotide sequence shown in SEQ ID NO:20.

7. A DNA comprising a DNA sequence which comprises a promoter region required for the expression of a recombinant protein in a prokaryote or eukaryote, the DNA sequence being attached at the 5' end of the DNA of claim 1.

8. The DNA of claim 7, wherein the DNA sequence which comprises a promoter region is derived from a bacterium belonging to the genus Bacillus.

9. The DNA of claim 8, wherein the DNA sequence which comprises a promoter region is derived from the CWP from a bacterium belonging to the genus Bacillus.

10. A vector containing the DNA of claim 7.

11. A host cell transformed with the vector of claim 10.

12. A bacterium belonging to the genus Bacillus which is transformed with the vector of claim 10.

13. The bacterium of claim 12, wherein the bacterium is *Bacillus brevis*.

14. A method for producing insulin, wherein the method comprises:

culturing the host cell of claim 11 or the bacterium of claim 12, in a culture medium, to express a fusion protein encoded by a DNA of interest in the host cell or bacterium;

collecting the fusion protein; and subjecting the fusion protein to an enzymatic cleavage treatment to isolate insulin.

15. The method of claim 14, wherein the fusion protein comprises an amino acid sequence shown in SEQ ID NO:21.

16. The method of claim 14, wherein the expressed fusion protein is separated and purified from the host cell or bacterium, or from the cultured medium.

17. The method of claim 14, wherein the enzymatic cleavage treatment is performed with thrombin or carboxypeptidase B.

18. A fusion protein comprising an amino acid sequence shown in SEQ ID NO:21.

* * * * *

SEQUENCE LISTING

```
<160> NUMBER OF SEQ ID NOS: 23

<210> SEQ ID NO 1
<211> LENGTH: 6
<212> TYPE: PRT
<213> ORGANISM: Artificial Sequence
<220> FEATURE:
<223> OTHER INFORMATION: Designated is an amino acid sequence capable of
      cleaving by thrombin.

<400> SEQUENCE: 1

Gly Ser Leu Gln Pro Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Designated is an amino acid sequence capable of
      cleaving by thrombin.

<400> SEQUENCE: 2

Arg Gly His Arg Pro
1               5

<210> SEQ ID NO 3
<211> LENGTH: 31
<212> TYPE: PRT
<213> ORGANISM: Homo sapiens

<400> SEQUENCE: 3

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 4
<211> LENGTH: 9
<212> TYPE: PRT
<213> ORGANISM: Bacillus brevis
<220> FEATURE:
<221> NAME/KEY: MISC_FEATURE
<222> LOCATION: (1)..(9)
<223> OTHER INFORMATION: J. Bacteriol. 169:1239-1245 (1989)

<400> SEQUENCE: 4
```

```
Ala Glu Glu Ala Ala Thr Thr Thr Ala
1               5
```

<210> SEQ ID NO 5
<211> LENGTH: 9
<212> TYPE: PRT
<213> ORGANISM: Bacillus brevis
<220> FEATURE:
<221> NAME/KEY: MISC_FEATURE
<222> LOCATION: (1)..(9)
<223> OTHER INFORMATION: J. Bacteriol. 170:176-186 (1988)

<400> SEQUENCE: 5

```
Ala Pro Lys Asp Gly Ile Tyr Ile Gly
1               5
```

<210> SEQ ID NO 6
<211> LENGTH: 9
<212> TYPE: PRT
<213> ORGANISM: Bacillus brevis
<220> FEATURE:
<221> NAME/KEY: MISC_FEATURE
<222> LOCATION: (1)..(9)
<223> OTHER INFORMATION: J. Bacteriol. 172:1312-1320 (1990)

<400> SEQUENCE: 6

```
Ala Glu Asp Thr Thr Thr Ala Pro Lys
1               5
```

<210> SEQ ID NO 7
<211> LENGTH: 20
<212> TYPE: DNA
<213> ORGANISM: Bacillus brevis
<220> FEATURE:
<221> NAME/KEY: misc_feature
<222> LOCATION: (1)..(20)
<223> OTHER INFORMATION: Yamagata, H. et al., 1987, J. Bacteriol. 169:
      1239-1245.

<400> SEQUENCE: 7
gtcgttaaca gtgtattgct                                              20

<210> SEQ ID NO 8
<211> LENGTH: 18
<212> TYPE: DNA
<213> ORGANISM: Bacillus brevis
<220> FEATURE:
<221> NAME/KEY: misc_feature
<222> LOCATION: (1)..(18)
<223> OTHER INFORMATION: Tsuboi et al., 1988, J. Bacteriol. 170:935-945.

<400> SEQUENCE: 8
agctgtagta gttgctgc                                                18

<210> SEQ ID NO 9
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Bell, G.I. et al., 1979, Nature 282:525-527.

<400> SEQUENCE: 9
atggccctgt ggatgcgcc                                               19

<210> SEQ ID NO 10

```
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Bell, G.I. et al., 1979, Nature 282:525-527.

<400> SEQUENCE: 10
ctagttgcag tagttctcc                                               19

<210> SEQ ID NO 11
<211> LENGTH: 18
<212> TYPE: DNA
<213> ORGANISM: Homo sapiens

<400> SEQUENCE: 11
tttgtgaacc aacacctg                                                18

<210> SEQ ID NO 12
<211> LENGTH: 36
<212> TYPE: DNA
<213> ORGANISM: Artificial Sequence
<220> FEATURE:
<223> OTHER INFORMATION: Designated is a forward primer for PCR to
      amplify a DNA fragment coding for GSLQPR-B chain-R.

<400> SEQUENCE: 12
ggttccttgc aacctcgttt tgtgaaccaa cacctg                            36

<210> SEQ ID NO 13
<211> LENGTH: 18
<212> TYPE: DNA
<213> ORGANISM: Homo sapiens

<400> SEQUENCE: 13
gcgggtcttg ggtgtgta                                                18

<210> SEQ ID NO 14
<211> LENGTH: 18
<212> TYPE: DNA
<213> ORGANISM: Homo sapiens

<400> SEQUENCE: 14
gaggcagagg acctgcag                                                18

<210> SEQ ID NO 15
<211> LENGTH: 18
<212> TYPE: DNA
<213> ORGANISM: Homo sapiens

<400> SEQUENCE: 15
ctgcagggac ccctccag                                                18

<210> SEQ ID NO 16
<211> LENGTH: 36
<212> TYPE: DNA
<213> ORGANISM: Artificial Sequence
<220> FEATURE:
<223> OTHER INFORMATION: Designated is a forward primer for PCR to
      amplify a DNA fragment coding for GHRP-Linker.

<400> SEQUENCE: 16
ggtcaccgtc cagaggcaga ggacctgcag gtgggg                            36
```

```
<210> SEQ ID NO 17
<211> LENGTH: 21
<212> TYPE: DNA
<213> ORGANISM: Homo sapiens

<400> SEQUENCE: 17
ggcattgtgg aacaatgctg t                                              21

<210> SEQ ID NO 18
<211> LENGTH: 27
<212> TYPE: DNA
<213> ORGANISM: Homo sapiens

<400> SEQUENCE: 18
ctagttgcag tagttctcca gctggta                                        27

<210> SEQ ID NO 19
<211> LENGTH: 27
<212> TYPE: DNA
<213> ORGANISM: Artificial Sequence
<220> FEATURE:
<223> OTHER INFORMATION: Designated is a forward primer for PCR to
      amplify a DNA fragment coding for PR-A chain.

<400> SEQUENCE: 19
ccacgtggca ttgtggaaca atgctgt                                        27

<210> SEQ ID NO 20
<211> LENGTH: 372
<212> TYPE: DNA
<213> ORGANISM: Artificial Sequence
<220> FEATURE:
<223> OTHER INFORMATION: Designated is a nucleotide sequence of DNA
      coding for MWPsp-MWPmp9-GSLQPR-B chain-RGHRP-Linker-PR-A chain.

<400> SEQUENCE: 20
gtcgttaaca gtgtattggc tagtgcactc gcacttactg ttgctccaat ggctttcgca    60
gcagaagaag cagcaactac tacagctggg tccctgcagc cacgttttgt gaaccaacac   120
ctgtgcggct cacacctggt ggaagctctc tacctagtgt gcggggaaag aggcttcttc   180
tacacaccca agacccgcgg tcaccgtcca gaggcagagg acctgcaggt ggggcaggtg   240 gagctggggcg ggggccctgg tgcaggcagc ctgcagccct ggccctgga ggggtccctg   300 cagccacgtg gcattgtgga acaatgctgt accagcatct gctccctcta ccagctggag   360
aactactgca ac                                                       372

<210> SEQ ID NO 21
<211> LENGTH: 124
<212> TYPE: PRT
<213> ORGANISM: Artificial Sequence
<220> FEATURE:
<223> OTHER INFORMATION: Designated is an amino acid sequence of
      MWPsp-MWPmp9- GSLQPR-B chain-RGHRP-Linker-PR-A chain.

<400> SEQUENCE: 21

Val Val Asn Ser Val Leu Ala Ser Ala Leu Ala Leu Thr Val Ala Pro
  1               5                  10                  15

Met Ala Phe Ala Ala Glu Glu Ala Ala Thr Thr Thr Ala Gly Ser Leu
                 20                  25                  30

Gln Pro Arg Phe Val Asn Gln His Leu Cys Gly Ser His Leu Val Glu
             35                  40                  45

Ala Leu Tyr Leu Val Cys Gly Glu Arg Gly Phe Phe Tyr Thr Pro Lys
         50                  55                  60
```

```
Thr Arg Gly His Arg Pro Glu Ala Glu Asp Leu Gln Val Gly Gln Val
 65                  70                  75                  80

Glu Leu Gly Gly Gly Pro Gly Ala Gly Ser Leu Gln Pro Leu Ala Leu
                 85                  90                  95

Glu Gly Ser Leu Gln Pro Arg Gly Ile Val Glu Gln Cys Cys Thr Ser
            100                 105                 110

Ile Cys Ser Leu Tyr Gln Leu Glu Asn Tyr Cys Asn
        115                 120

<210> SEQ ID NO 22
<211> LENGTH: 6
<212> TYPE: PRT
<213> ORGANISM: Artificial Sequence
<220> FEATURE:
<223> OTHER INFORMATION: Designated is an amino acid sequence capable of
      cleaving by thrombin.  See SEQ ID NO:1.
<220> FEATURE:
<221> NAME/KEY: MISC_FEATURE
<222> LOCATION: (2)..(2)
<223> OTHER INFORMATION: Xaa = Ser; possible substitutions are Val, Glu,
      Phe, Asp, Pro, Ile, Gly, Lys, Arg, Ala, Gln, Asn, or Leu
<220> FEATURE:
<221> NAME/KEY: MISC_FEATURE
<222> LOCATION: (3)..(3)
<223> OTHER INFORMATION: Xaa = Leu; possible substitutions are Arg, Val,
      Phe, Asp, Gly, Leu, His, Ile, Met, Thr, or Lys
<220> FEATURE:
<221> NAME/KEY: MISC_FEATURE
<222> LOCATION: (4)..(4)
<223> OTHER INFORMATION: Xaa = Gln; possible substitutions are Gln, Phe,
      Tyr, Gly, Ile, Asn, Ala, Arg, Thr, Ser, Leu, Val, or Cys
<220> FEATURE:
<221> NAME/KEY: MISC_FEATURE
<222> LOCATION: (5)..(5)
<223> OTHER INFORMATION: Xaa = Pro; possible substitutions are Ala or
      Val
<220> FEATURE:
<221> NAME/KEY: MISC_FEATURE
<222> LOCATION: (6)..(6)
<223> OTHER INFORMATION: Xaa = Arg; possible substitution is Lys
<220> FEATURE:
<221> NAME/KEY: MISC_FEATURE
<222> LOCATION: (1)..(6)
<223> OTHER INFORMATION: Chang, J-Y, 1985, Eur. J. Biochem. 151:217-224.
      Kawabata et al., 1988, Eur. J. Biochem. 172:17-25.

<400> SEQUENCE: 22

Gly Xaa Xaa Xaa Xaa Xaa
 1               5

<210> SEQ ID NO 23
<211> LENGTH: 5
<212> TYPE: PRT
<213> ORGANISM: Artificial Sequence
<220> FEATURE:
<223> OTHER INFORMATION: Designated is an amino acid sequence capable of
      cleaving by thrombin.  See SEQ ID NO:2.
<220> FEATURE:
<221> NAME/KEY: MISC_FEATURE
<222> LOCATION: (1)..(1)
<223> OTHER INFORMATION: Xaa = Arg; possible substitution is Lys
<220> FEATURE:
<221> NAME/KEY: MISC_FEATURE
<222> LOCATION: (2)..(2)
<223> OTHER INFORMATION: Xaa = Gly; possible substitutions are Thr, Ile,
      His, Ser, Ala, Phe, Val, Asn, Asp, Leu, or Pro
<220> FEATURE:
<221> NAME/KEY: MISC_FEATURE
<222> LOCATION: (3)..(3)
<223> OTHER INFORMATION: Xaa = His; possible substitutions are Pro, Trp,
      Cys, Gln, Thr, Ser, Val, Leu, Ala, Phe, or Gly
<220> FEATURE:
```

-continued

```
<221> NAME/KEY: MISC_FEATURE
<222> LOCATION: (4)..(4)
<223> OTHER INFORMATION: Xaa = Arg; possible substitutions are Val, Pro,
      Glu, Asn, Asp, Ser, Met, Lys, Ala, Gln, Gly, Trp, or Thr
<220> FEATURE:
<221> NAME/KEY: MISC_FEATURE
<222> LOCATION: (5)..(5)
<223> OTHER INFORMATION: Xaa = Pro; possible substitutions are Val, Thr,
      Leu, Ser, Asp, Gly, Tyr, Ile, Asn, Arg, His, or Glu
<220> FEATURE:
<221> NAME/KEY: MISC_FEATURE
<222> LOCATION: (1)..(5)
<223> OTHER INFORMATION: Chang, J-Y, 1985, Eur. J. Biochem. 151:217-224.

<400> SEQUENCE: 23

Xaa Xaa Xaa Xaa Xaa
1               5
```